(12) United States Patent
Krupp et al.

(10) Patent No.: US 11,369,379 B2
(45) Date of Patent: Jun. 28, 2022

(54) HAIR GRASPING DEVICE

(71) Applicant: TLA M.D., LLC, North Liberty, IA (US)

(72) Inventors: David Carl Krupp, North Liberty, IA (US); Kathleen Bartel, Rockford, IL (US); Maddie Dietz, Los Angeles, CA (US); Alyssa Esquivel, Kansas City, MO (US); Tracy Piplani, St. Paul, MN (US); Charles E. Romans, North Liberty, IA (US)

(73) Assignee: 11:11, LLC, North Liberty, IA (US)

(*) Notice: Subject to any disclaimer, the term of this patent is extended or adjusted under 35 U.S.C. 154(b) by 114 days.

(21) Appl. No.: 16/245,477

(22) Filed: Jan. 11, 2019

(65) Prior Publication Data

US 2019/0223869 A1 Jul. 25, 2019

Related U.S. Application Data

(63) Continuation-in-part of application No. 15/949,957, filed on Apr. 10, 2018.

(Continued)

(51) Int. Cl.
*A61B 17/08* (2006.01)
*A61B 17/28* (2006.01)
*A61B 17/00* (2006.01)

(52) U.S. Cl.
CPC .............. *A61B 17/08* (2013.01); *A61B 17/28* (2013.01); *A61B 17/00491* (2013.01);

(Continued)

(58) Field of Classification Search
CPC .......... A61B 2017/00752; A61B 2018/00476; A61B 17/29; A61B 2017/2926;

(Continued)

(56) References Cited

U.S. PATENT DOCUMENTS 3,541,591 A 11/1970 Hoegerman
3,735,765 A * 5/1973 Ichelson ................ A61B 17/08
606/135

(Continued)

FOREIGN PATENT DOCUMENTS

EP 1164887 1/2004
GB 449001 6/1936

(Continued)

OTHER PUBLICATIONS

PCTUS1826950 Written Opinion of the International Searching Authority—dated Aug. 24, 2019.
Dec. 2, 2020 Search Report PCTUS2018026950.

*Primary Examiner* — Darwin P Erezo
*Assistant Examiner* — Brigid K Byrd
(74) *Attorney, Agent, or Firm* — Nyemaster Goode, P.C.

(57) ABSTRACT

A hair grasping device having a handle with hollow fingers, a trigger slidably attached to the handle, a number of grips slidably attached within the hollow fingers connected to the trigger. Each of the grips has a first and a second arm, a central post, and an extended position and retracted position. When in the retracted position, the arms are forced against the central post by the hollow fingers, and when in the extended position, the arms are forced away from the central post, creating a clearance between the arms and the central post.

15 Claims, 26 Drawing Sheets

Related U.S. Application Data

(60) Provisional application No. 62/483,627, filed on Apr. 10, 2017.

(52) U.S. Cl.
CPC ............... *A61B 2017/00349* (2013.01); *A61B 2017/081* (2013.01); *A61B 2017/088* (2013.01)

(58) Field of Classification Search
CPC ...... A61B 2017/2944; A61B 2017/295; A61B 17/10; A61B 2017/00349; A61B 17/28; A61B 17/08; A45D 26/0023; A45D 26/0042

See application file for complete search history.

(56) References Cited

U.S. PATENT DOCUMENTS

| | | | |
|---|---|---|---|
| 4,240,435 A * | 12/1980 | Yazawa | A45D 26/0071 294/99.2 |
| 4,994,061 A | 2/1991 | McPherson | |
| 5,176,703 A | 1/1993 | Peterson | |
| 5,281,237 A | 1/1994 | Gimpelson | |
| 5,474,057 A | 12/1995 | Makower et al. | |
| 5,613,937 A | 3/1997 | Garrison et al. | |
| 5,618,307 A | 4/1997 | Donlon et al. | |
| 6,254,624 B1 * | 7/2001 | Oddsen | A61B 17/08 606/150 |
| 6,973,931 B1 | 12/2005 | King | |
| 8,322,353 B2 | 12/2012 | Russell | |
| 8,770,207 B2 | 7/2014 | Takagi | |
| 8,920,442 B2 | 12/2014 | Sibbitt et al. | |
| 2010/0185213 A1 | 7/2010 | Lam | |
| 2011/0077668 A1 * | 3/2011 | Gordon | A61B 17/0057 606/142 |
| 2017/0013928 A1 | 1/2017 | Debenedictis et al. | |
| 2018/0289373 A1 | 10/2018 | Krupp et al. | |

FOREIGN PATENT DOCUMENTS

| | | |
|---|---|---|
| GB | 962626 | 7/1964 |
| WO | 2007112072 | 10/2007 |

* cited by examiner

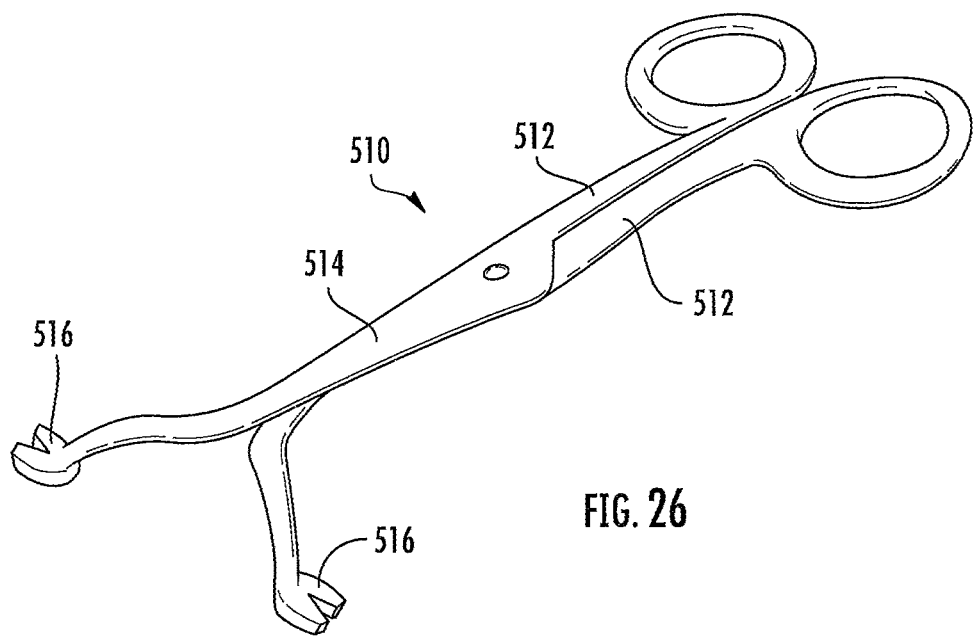
FIG. 26
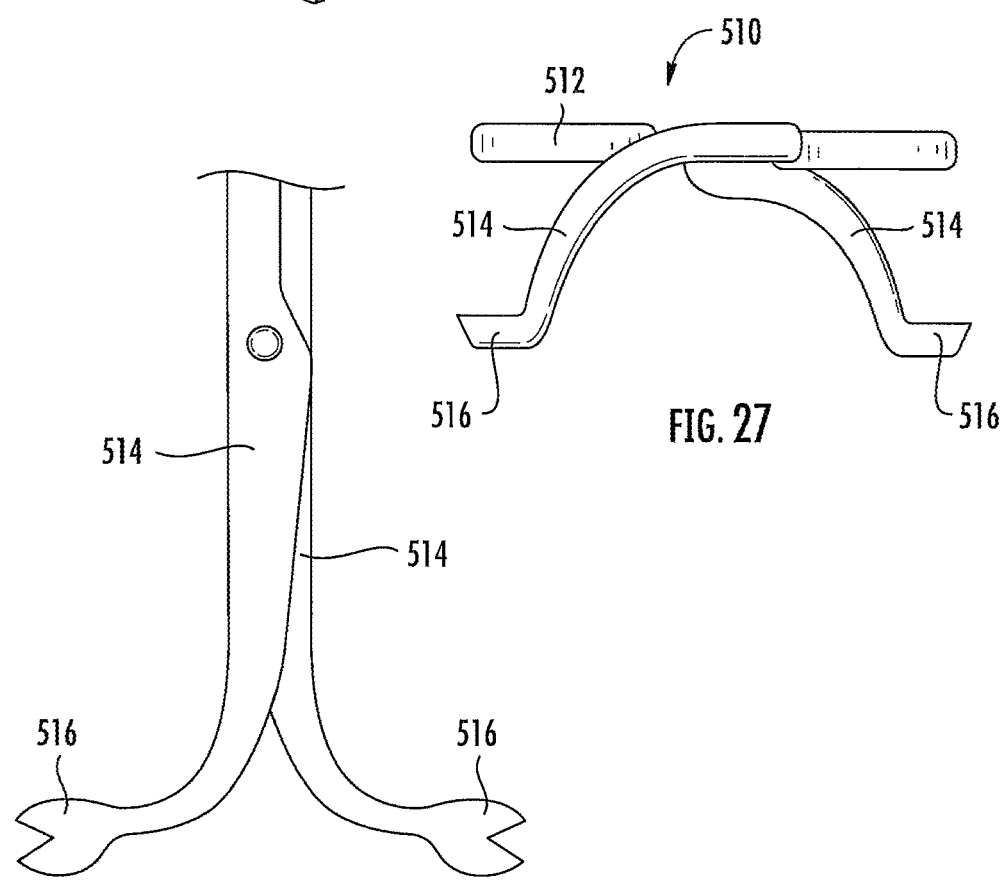
FIG. 27
FIG. 28

HAIR GRASPING DEVICE

CROSS REFERENCE TO RELATED APPLICATIONS

This Application is a Continuation-in-Part of and claims priority to U.S. patent application Ser. No. 15/949,957, filed Apr. 10, 2018, entitled "HAIR GRASPING DEVICE," which is pending, which application is based upon U.S. Provisional Application Ser. No. 62/483,627 filed Apr. 10, 2017, the complete disclosures of which are hereby expressly incorporated by reference.

BACKGROUND OF THE DISCLOSURE

An estimated 7.3 million lacerations are seen in emergency departments and other clinics in the United States every year. Approximately 800,000 of these are scalp lacerations. Currently, the most common methods for closing scalp lacerations are sutures and staples. However, both these approaches require local anesthetics, are painful for the patient, and often require a follow-up visit for their removal. There is a less common known technique for closure of a scalp laceration that is non-invasive and requires no anesthetics and no follow-up visit. This method is known as the hair apposition technique (HAT). The hair apposition technique utilizes the patient's own hair to close the wound. Although the HAT overcomes some of the drawbacks of sutures and staples, the HAT can be difficult and time consuming for medical professionals since it can be hard to grasp and pull clusters of hair across the wound. There is therefore a need for a device which grabs and pulls hair across a wound to simplify the HAT.

SUMMARY OF THE PRESENT DISCLOSURE

One aspect of the present disclosure includes a hair grasping device having a handle with hollow fingers, a trigger slidably attached to the handle, a number of grips slidably attached within the hollow fingers connected to the trigger. Each of the grips has a first and a second arm, a central post, and an extended position and retracted position. When in the retracted position, the arms are forced against the central post by the hollow fingers, and when in the extended position, the arms are forced away from the central post, creating a clearance between the arms and the central post.

Another aspect of the present disclosure includes a hair grasping device with a handle having a hollow fingers, a trigger slidably attached to the handle, a number of grips each within the hollow fingers and operably attached to the trigger. The grips have first and second arms, an extended position, and a retracted position. When the grips are in the retracted position, the arms are urged against each other by the hollow fingers, and when the grips are in the extended position, the arms are urged away from each other, creating a clearance between the first arm and the second arm.

Another aspect of the present disclosure includes a method of grabbing and pulling hair away from an area of skin with a laceration, including capturing hair between a pair of arms of a grip while the pair of arms are in an open position, sliding the pair of arms into an internal opening within a hollow finger of a hair grasping device by sliding a trigger on a handle on the hair grasping device from a released position to a grasping position, ensnaring the hair by urging the pair of arms to a closed position by retracting the pair of arms within the hollow finger, and holding the amount or hair by exerting a pinching force on the arms by the internal opening.

These and other aspects, objects, and features of the present disclosure will be understood and appreciated by those skilled in the art upon studying the following specification, claims, and appended drawings.

BRIEF DESCRIPTION OF THE DRAWINGS

In the drawings:

FIG. 26 is an isometric view of the hair grasping device shown in FIG. 24 in the hair holding position.

FIG. 27 is an end view of the hair grasping device shown in FIG. 24.

FIG. 28 is a close up side view of the grips and fingers of the device shown in FIG. 24.

DETAILED DESCRIPTION OF EMBODIMENTS

Figure 1:
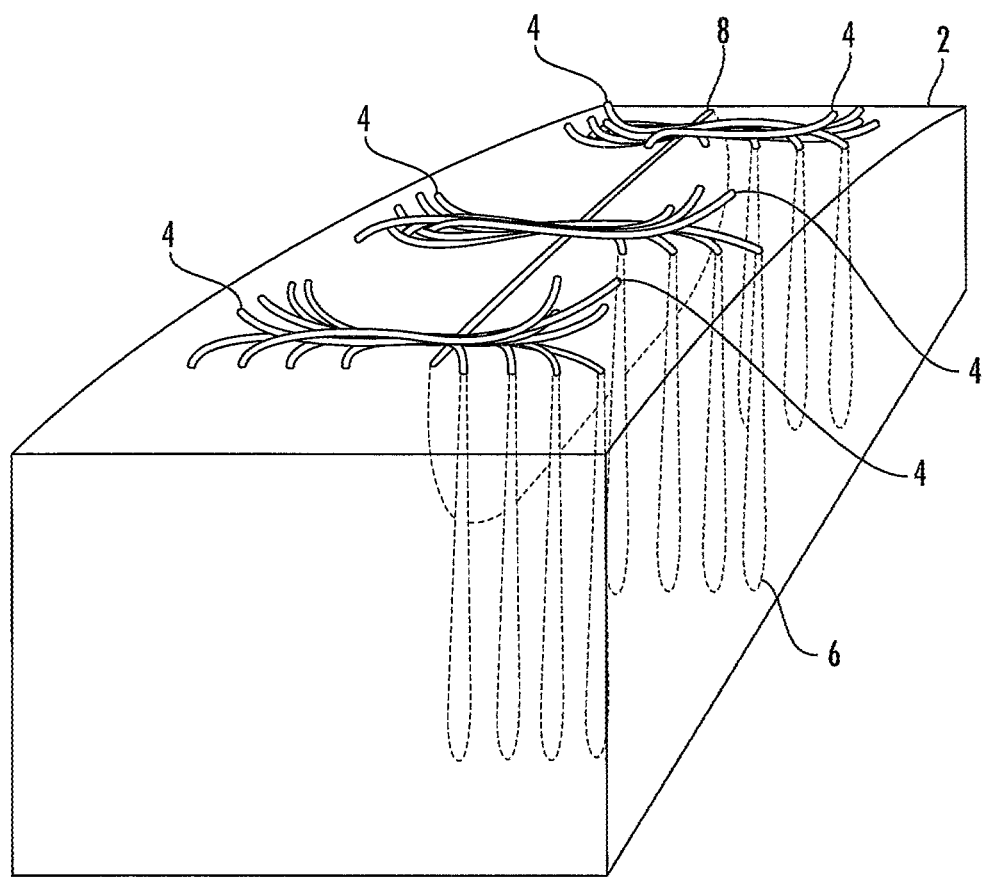
FIG. 1 is a diagram showing a wound closed using the hair apposition technique.

Described herein are various configurations and designs for a device that grabs hair 4 and holds it in tension, such as a hand held tool for, in some instances, closing lacerations. The following description and drawings sufficiently illustrate specific examples to enable those skilled in the art to practice them. Other examples may incorporate structural and other changes. Portions and features of some examples may be included in, or substituted for, those of other examples. As used within this description, corresponding portions of differing embodiments will be shown using similar reference numerals with a different numeral in the hundreds place.

FIG. 1 shows the end result of a laceration 8 which has been closed using the apparatus as described. A person or animal may incur some injury that causes a laceration 8 on a patch of skin 2 that is surrounded by some hair 4. An example of this is on the scalp of a person's head. Instead of using a sutures, staples, stitches, or some other form of closing the wound that requires anesthetics and follow-up, the person's own hair 4 is used to pull the skin on either side of the wound 8 together. The hair 4 is pulled across the wound 8 and then closed using an adhesive glue, tying the hair 4 together, or held together in some other fashion to hold the wound 8 closed.

Figure 2A:
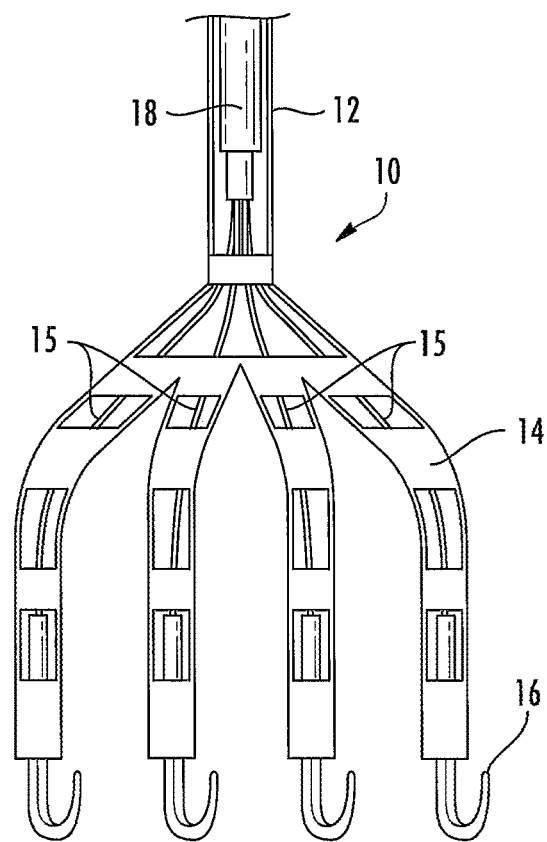
FIG. 2A is a bottom view of the hair grasping device of an embodiment.
Figure 2B:
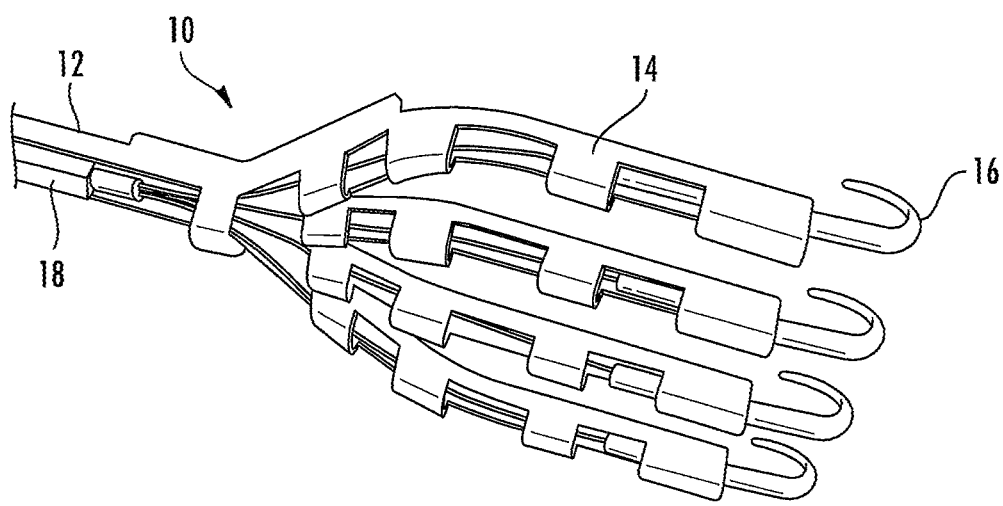
FIG. 2B is an isometric view of the hair grasping device shown in FIG. 2A.

Turning now to FIGS. 2A-2B, a hair grasping device 10 is shown having a handle 12, a plurality of spaced apart fingers 14, a plurality of hair grips such as hooks 16, and a trigger 18. A trigger as used in the disclosure is any design feature that aids a user in manipulating the movable parts of the device. The handle 12 may have an opening therein to allow the trigger 18 and any associated mechanics necessary to slide within it. As described in more detail below, various embodiments of the device 10 include different types of hair grips. The hair grips may include hooks 16 (FIGS. 2A-8), pincers 116 (FIGS. 9-12), vacuum, tape, hook and loop fasteners, screw 216 (FIGS. 13-16), and chemical attachment. The fingers 14 may also have openings therein to allow the hair grips to move with respect to the fingers 14. As shown, there are four fingers 14 and four hooks 16 associated with the fingers 14. It should be known that there may be three fingers 14 and hooks 16, or five fingers 14 and hooks 16, or any other number of fingers 14 and hooks 16 that a user deems is most efficient use of the space and most appropriate for the size/length of the laceration 8.

Figure 3:
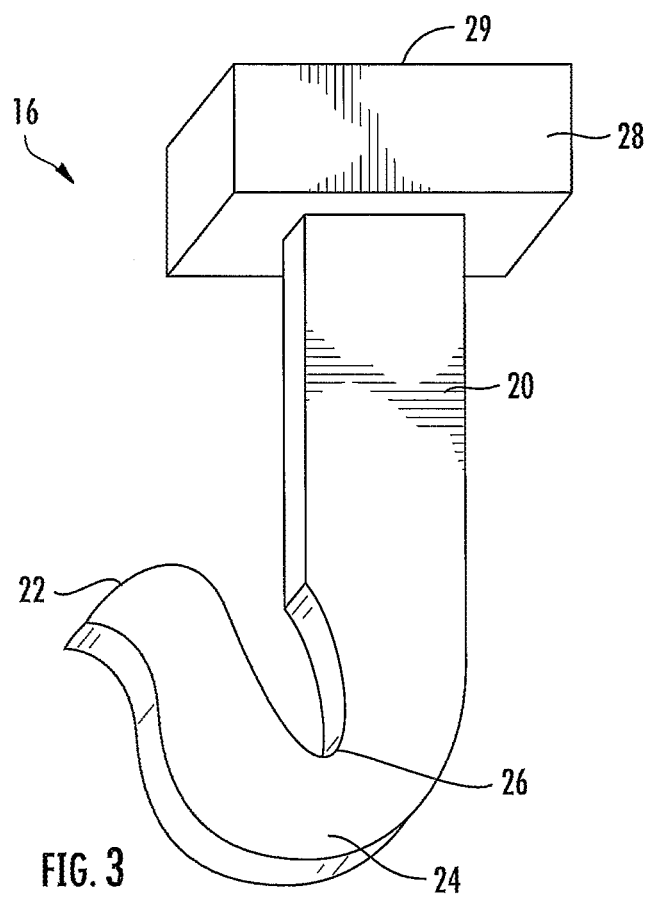
FIG. 3 is a detailed isometric view of a hook of an embodiment.
Figure 4:
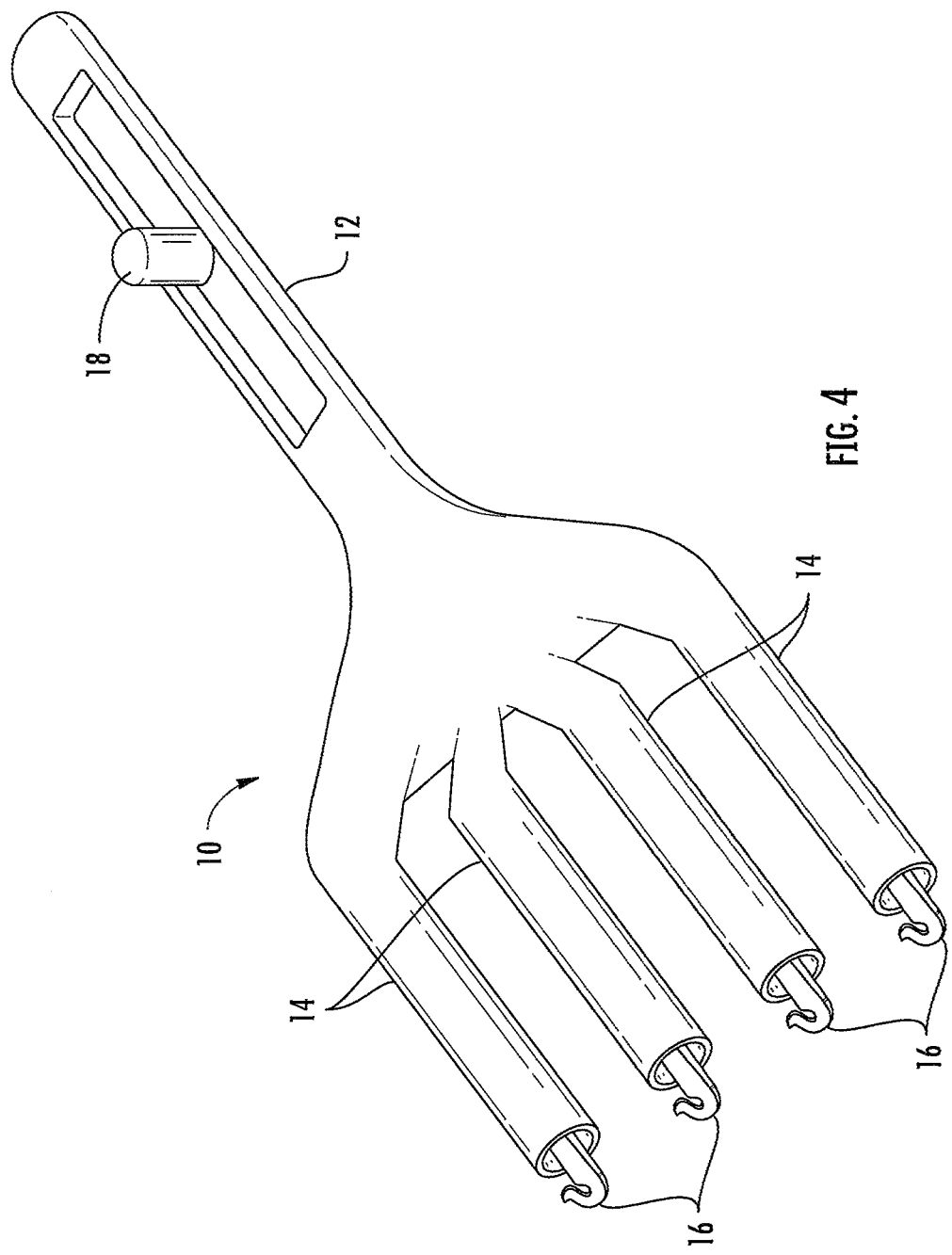
FIG. 4 is an isometric view of another embodiment of the hair grasping device.
Figure 5A:
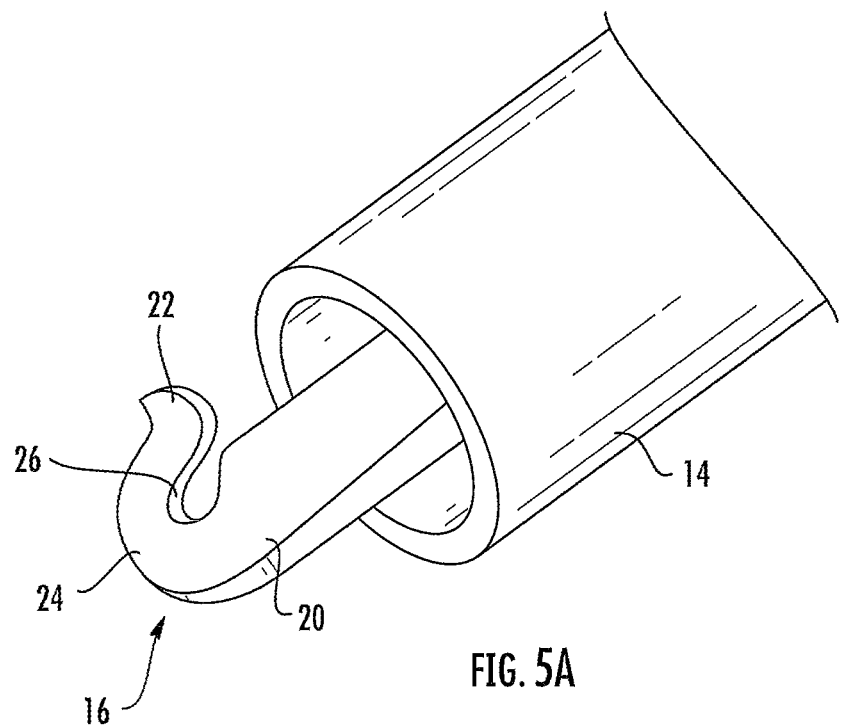
FIG. 5A is a close up isometric view of the finger and hook arrangement of the device shown in FIG. 4 in the hair grasping position.
Figure 5B:
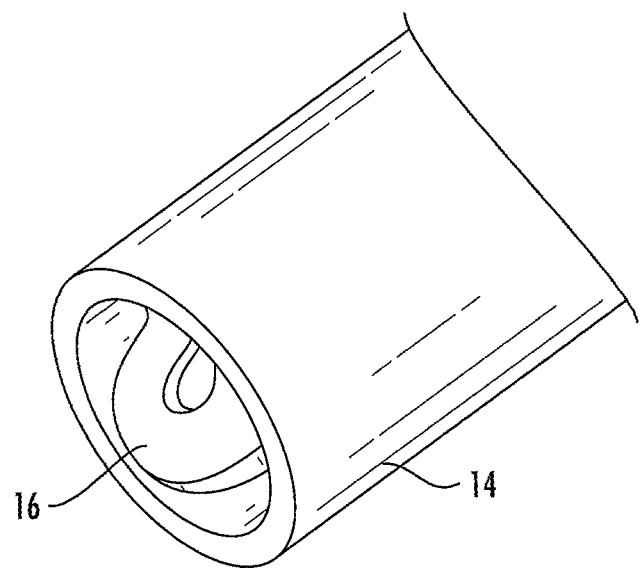
FIG. 5B is a close up isometric view of the finger and hook arrangement of the device shown in FIG. 4 in the hair holding position.
Figure 6:
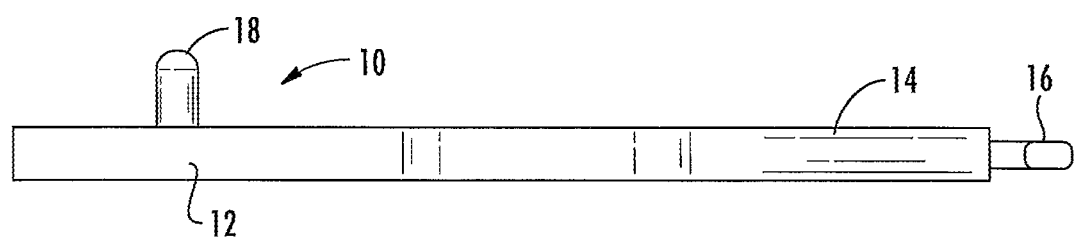
FIG. 6 is a side view of another embodiment of the hair grasping device.
Figure 7:
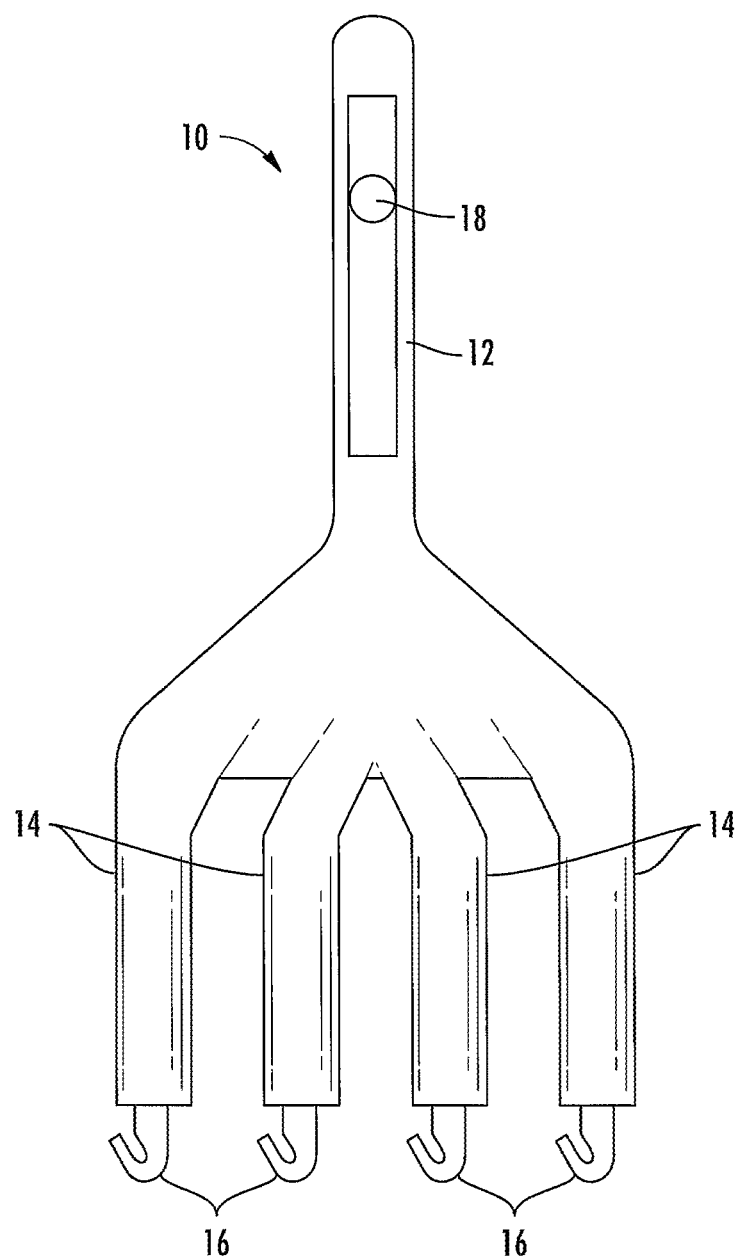
FIG. 7 is a top view of the hair grasping device shown in FIG. 6.

FIG. 3 shows the hook 16 of this particular embodiment in more detail. The hook 16 may include a base 20, a tip 22, and a bend 24. The hook 16 may have a throat 26 that is sized to grasp and hold a certain amount of hair 4. The hook 16 may also have a connection portion 28 that allows the hook 16 to be connected to a cable 15 (FIGS. 2A & 2B). The cable 15 can be comprised of, but is not limited to, stainless steel, titanium, nitinol, nylon. The connection portion 28 may also be sized and shaped such that it allows a landing 29 for a spring (not shown) which may bias the grasping mechanism in the hair grasping position.

In the embodiment of FIGS. 2A-8, a user may grab the device 10 by the handle 12. The user may hold the device 10 with the handle 12 on one side of the laceration 8 and with the fingers 14 reaching across and to the opposite side of the laceration 8. The hair grips shown in FIGS. 2A-8 are hooks 16, which are placed such that the hooks 16 grab an amount of hair 4 from the opposite side of the laceration 8. The hooks are in a hair grasping position with tip 22, bend 24, and throat 26 open to grasp an amount of hair 4.

Figure 2C:
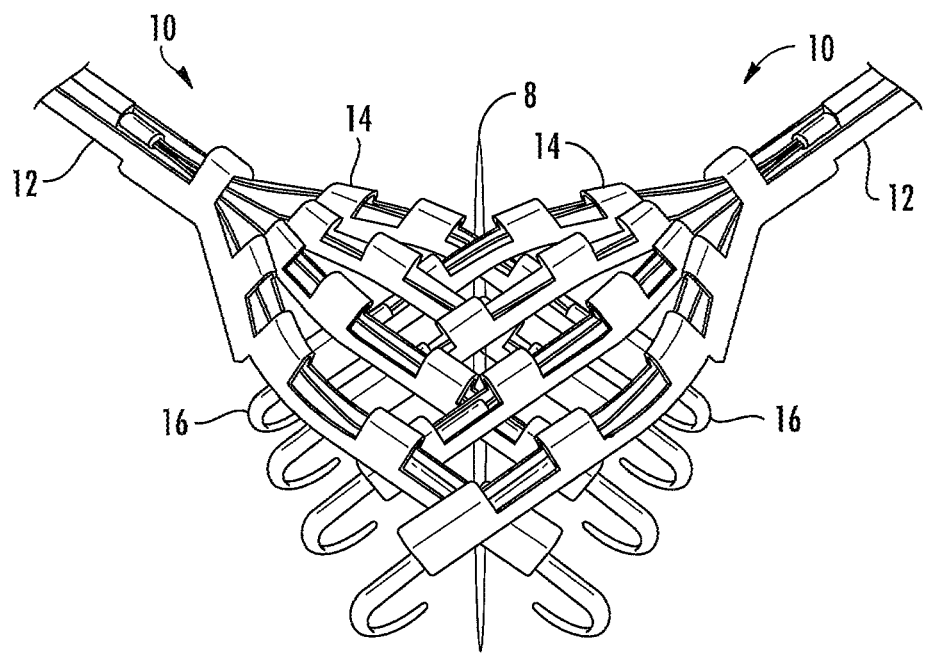
FIG. 2C is an isometric view of two devices of an embodiment being used simultaneously.

Once an amount of hair 4 has been grasped by the hooks 16, the user may then actuate a trigger 18 within the handle 12 to pull the hooks 16 from the hair grasping position to a hair holding position. A cable 15 has a first end combined with the trigger 18 and a second end combined with the hooks 16. The cable 15 may extend through openings in the handle 12 and fingers 14. As the user moves the trigger 18 in a direction away from the fingers 14, the hooks 16 are pulled by the cable 15 to correspondingly move in the same direction. This movement of the hooks 16 is such that the tips 22 are operably coupled with the end of the fingers 14 into a hair holding position. Operably coupled in this respect means that the tips 22 and the fingers 14 interact to help prevent the amount of hair 4 from escaping the hook 16. In this embodiment, the base 20 of the hook 16 is substantially inserted within the finger 14, but the bend 24 and the tip remain on the outside of the finger 14, essentially holding the hair 4 between the end of the finger 14 and the throat 26 of the hook 16. There may further be a spring (not shown) within the fingers 14 that urges the hook 16 back into the hair grasping position when the trigger 18 is released. The spring may have an end that rests on the landing 29 of the hook 16. As shown in FIG. 2C, in some embodiments two devices 10 may be used at the same time to contemporaneously grab and pull hair 4 across the wound from opposite sides of the laceration 8. Further, the finger 14 may also include a cutting mechanism such as a blade (not shown). As the hook is pulled into the finger 14, the hair 4 may be pulled against the blade, thereby cutting the hair 4 at that point. The cutting blade may be disposed within the finger 14 in such an area as to be not accessible by a user's fingers in normal use.

The handle and extrusions can be made from any suitable material, including stainless steel, UHMWPE, PTFE, PVC, PET, Polyethylene, cloth, and fiber. Further, the trigger 18 may also include a latch which secures the trigger 18 in its actuated position without the user needing to hold it in the hair holding position. This makes it easier for the user to apply glue or other material to the laceration 8.

FIGS. 4-7 show another embodiment. The basic structure and use of the device 10 is similar to the previous embodiment. However, in this embodiment the interaction between the hooks 16 and the fingers 14 may be that the tips of the hooks 16 are fully inserted within the fingers 14 in the hair holding position as shown in FIG. 5B. A portion of the hair 4 is between the hook 16 and the inside wall of the fingers 14 so that the hair 4 is held in place by the tension between the hook 16) and the inside wall of the fingers 14. There may also be a pin or other feature (not shown) inside the fingers 14 which offers the opposing force with the hook 16. FIG. 5A shows the hook 16 in the hair grasping position, and FIG. 5B shows the hook 16 in the hair holding position.

Figure 8:
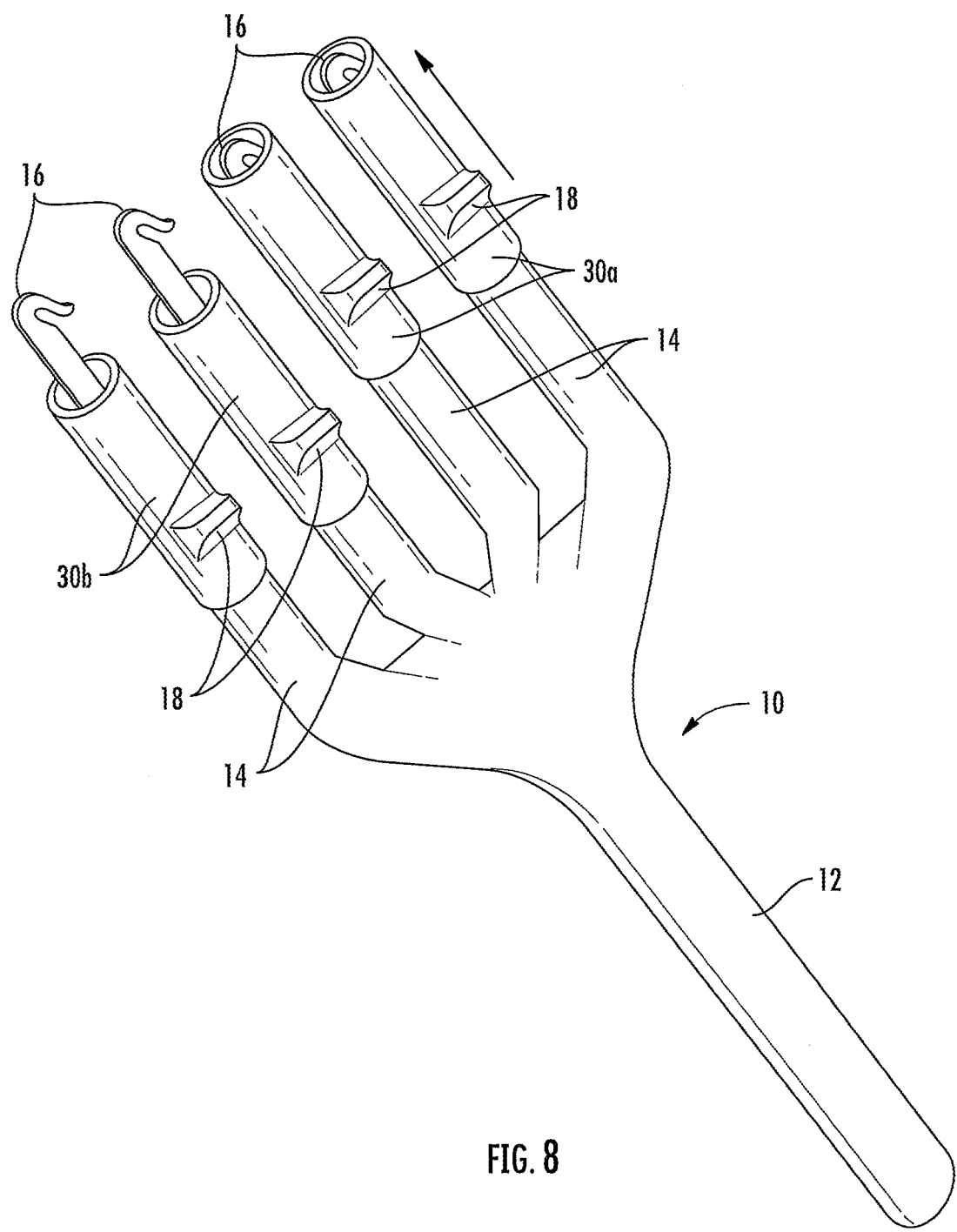
FIG. 8 is an isometric view of another embodiment of the hair grasping device.

Turning now to the embodiment shown in FIG. 8, the fingers 14 and the hooks 16 are stationary with respect to one another. In this embodiment, neither the handle 12 nor the fingers 14 need to be hollow. The fingers 14 may have an extrusion 30 slidably disposed over the fingers 14. The extrusions 30 may each have independent triggers 18 on them. These individual triggers 18 may be a separate piece attached to the extrusion 30, or may be created integrally with the extrusion 30. In this embodiment, extrusions 30*a* are in the hair holding position and extrusions 30*b* are in the hair grasping position. The user may grab an amount of hair 4 with the hooks 16 exposed and the extrusions 30 in the hair grasping position, and then use the triggers 18 to move the extrusions 30 to the hair holding position, with the hair being held in place with tension between the hooks 16 and the inside wall of the extrusion 30. In another embodiment, extrusion 30 may not be a hollow piece at all, but rather may be a flat, slidable piece and not encircle the hook 16. The hair may be held within the hook 16 and against the flat extrusion 30 and held in place.

Figure 9:
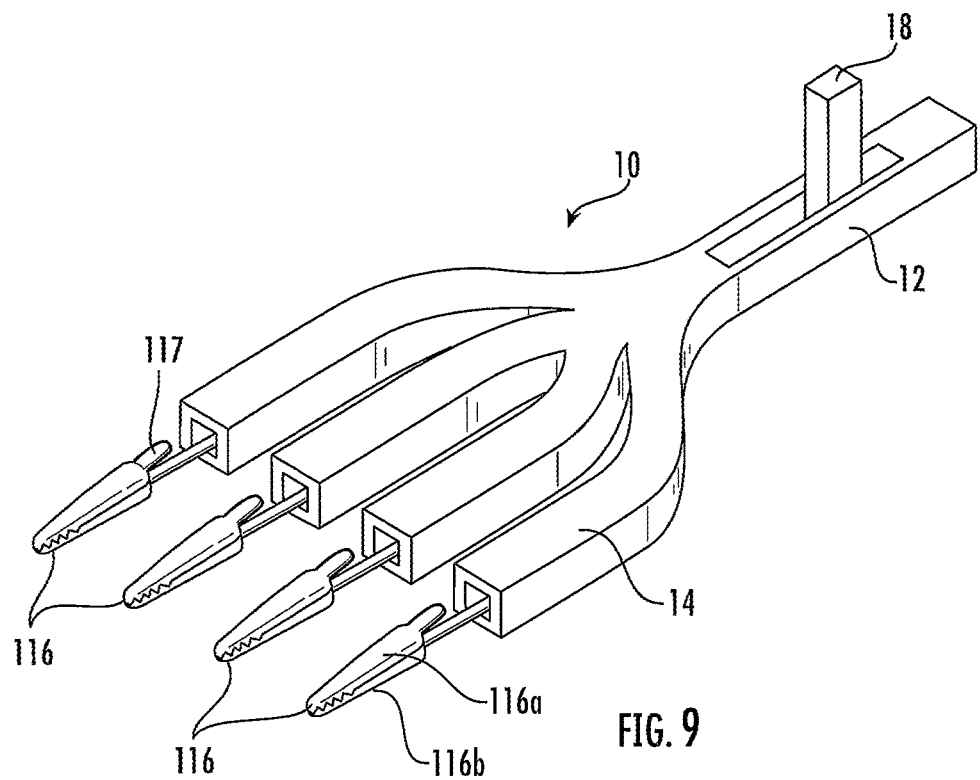
FIG. 9 is an isometric view of the hair grasping device of still another embodiment.
Figure 10:
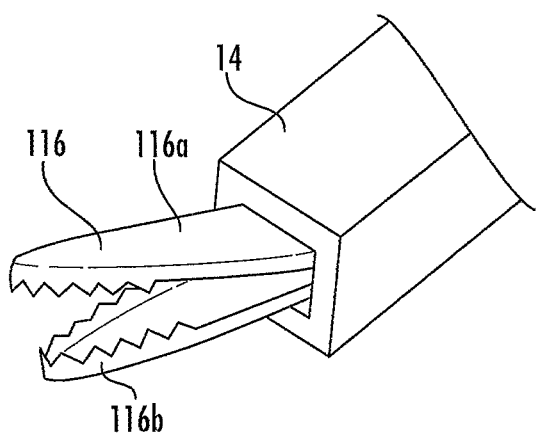
FIG. 10 is a close up isometric view of the finger and hook arrangement of the device shown in FIG. 9 in the hair grasping position.

FIGS. 9 and 10 show another embodiment of the hair grasping device 10. The basic configuration of the handle 12 and fingers 14 is similar to that described above. In this embodiment, the hair grip is an alligator clip 116. In this example, the hair grasping position and the hair holding positions may be reversed from the above embodiment. As shown in FIGS. 9 and 10, the alligator clips 116 may include an upper arm 116*a* and a lower arm 116*b*. The upper arm may further have a lever arm 117.

In the hair grasping position, lever arm 117 is forced to a closed position by the inner wall of the finger 114. When the lever arm 117 is forced closed, the arms 116*a* and 116*b* are correspondingly forced open. This allows the user to capture an amount of hair 4 of the user between the arms 116*a* and 116*b*. In the embodiment shown in FIG. 9, a trigger 18 is disposed in the handle 12 of the device 10 (similar to FIGS. 4, 7, and 9) to extend and retract the clips 116 between their hair grasping position and their hair holding positions. However in this embodiment, the structure must be such that pushing the trigger 18 toward the fingers 14 also pushes the grips 116 in the same direction. A cable 15 (not shown) is used as before, but the opening within which it is moved must be constrained enough to allow the compressive force on the cable 15 (not shown) to be delivered to similar movement by the grip 116. Alternatively, a material that is not a cable that allows for the transmission of compressive force is used, or any other mechanism that allows for the linear movement of the trigger 18 to be transmitted to the clips 116 may also be used.

Once the grips 116 are pushed far enough out of the fingers 14 so that the lever arms 117 are no longer constrained by the inner wall of the fingers 14, the arms 116*a* and 116*b* are urged closed to their hair holding position by a biasing force within the clips 116, such as a spring. The clips 116 are adapted to hold any hair 4 captured between the arms 116*a*, 116*b*. The lever arm 117 may further have a downward ramp (not shown) which allows for the alligator clips 116 to be pulled back to their hair grasping position within the fingers 14 and release the captured hair without needing to individually open each clip 116 before reinserting them into the fingers 14.

FIGS. 11A-12E show another embodiment closely related to that shown in FIGS. 9 and 10. In this embodiment the grips 616 have a pair of individual arms 616*a* and 616*b*. Whereas in the previous embodiment the grips are closed when they are extended from the fingers 14, in this embodiment the grips 616 are in the open position when they are extended from the fingers 14, and closed when retracted into fingers 14. The hollow fingers may have an internal opening that is wide enough to allow the arms 616*a* and 616*b* to slide within, but narrow enough that the arms 616*a* and 616*b* are forced closed upon themselves and exert slight pinching force to allow hair holding.

Figure 11A:
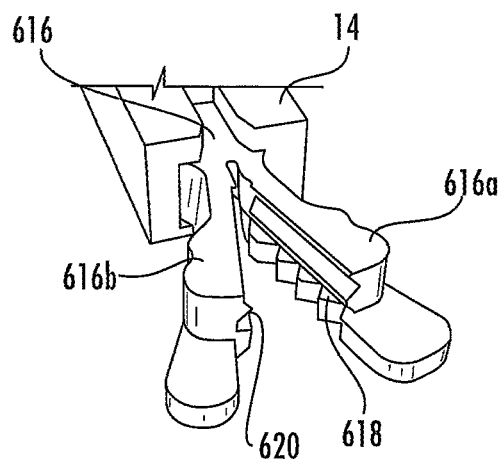
FIG. 11A is a close up isometric view of the finger and hook arrangement of the device shown in FIG. 9 in the hair grasping position.
Figure 11B:
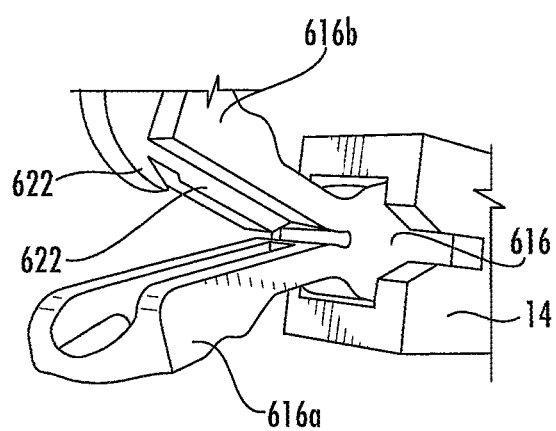
FIG. 11B is a close up isometric view of the finger and hook arrangement of the device shown in FIG. 9 in the hair holding position.

There may be a biasing element such as a spring that urges the grips 616 into the extended position, while pulling on the trigger 18 retracts the grips 616 into the fingers 14 and into the closed position. FIGS. 11A and 11B show additional pinching or grasping elements. FIG. 11A shows a combination of corresponding teeth 620 on each of arms 616*a* and 616*b*, and a corresponding tongue and groove 620. FIG. 11B shows the use of a different tongue and groove 622 and a hook 622 at a distal end of the arm to more easily grab hair. Using grips 616 having different holding and pinching shapes along different planes causes the hair 4 to change direction within the grip 616. This helps hold the hair more firmly since the gripping force increases as the hair 4 is pinched between surfaces on opposite arms 616*a*, 616*b*. These and any other similar features can be combined on the arms in any fashion to increase the grasping force of the device.

Similarly, FIGS. 12A-12E disclose yet another hinged configuration that may open and close upon extension and retraction and include arms 716*a* and 716*b*. In this embodiment, the fingers do not close upon themselves, but rather each arm 716*a*, 716*b* closes against a center post 716*c*. The arms 716*a* 716*b* may include a pinching plane that abuts a corresponding pinching plane on the center post 716*c*. The handle may include notches or detents for different phases of hair grasping. The detents may be at a first or open position where the hair stays between arms 716*a* and 716*b* and the post 716*c*, a partially closed position where the hair stays between the arms and the post, but can still slide to allow the user to position the handle to later cross over the wound, and a fully closed position to secure and pinch the hair and pull across the wound. The notches, grooves, or other detents can be placed in all three positions, or in any combination along with trigger end points.

The center post may have also have a shelf 716*d*, and the arms 716*a*, 716*b* may also include a corresponding shelf. In this embodiment, the hair is grabbed between the arms 716*a*, 716*b* and the center post 716*c*. As the user then pulls the trigger 18, the grips 716 are retracted into fingers 14, and the arms are squeezed together against the center post 716c. The corresponding shelves 716d on the arms 716a, 716b and the center post 716c add second and third planes of grip on arms 716a and 716b to hold the hair more firmly. As shown, the hinges that the arms rotate about are "living hinges." A living hinge is one in which the material itself operates as the rotational point typically by reducing thickness in the hinge area. However, other types of hinges are contemplated and within the skill in the art. Grips 716 are shaped to lift hair away from the scalp if wet, and also may include slight scoops or spatulas on the tips of arms 716a & 716b so they lift hair better during the retraction process.

Figure 12A:
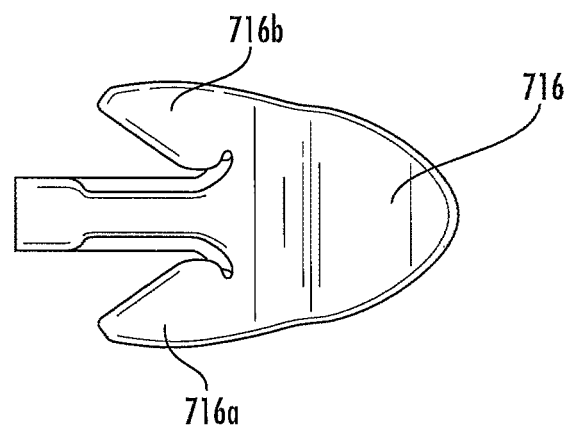
FIG. 12A is an isometric view of another embodiment of the hair grasping device.
Figure 12B:
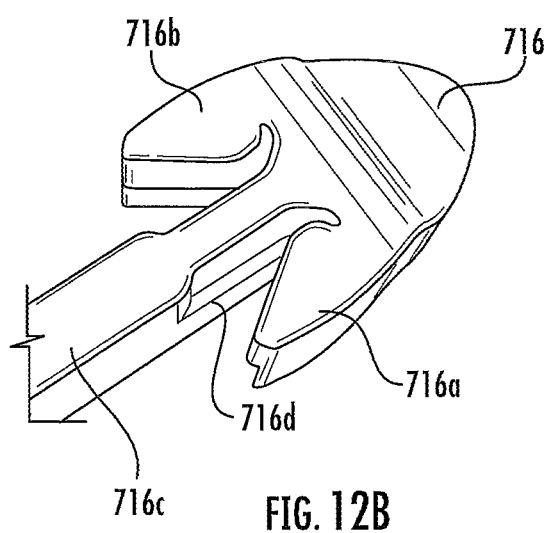
FIG. 12B is an isometric view of the hair grasping device of another embodiment.
Figure 12C:
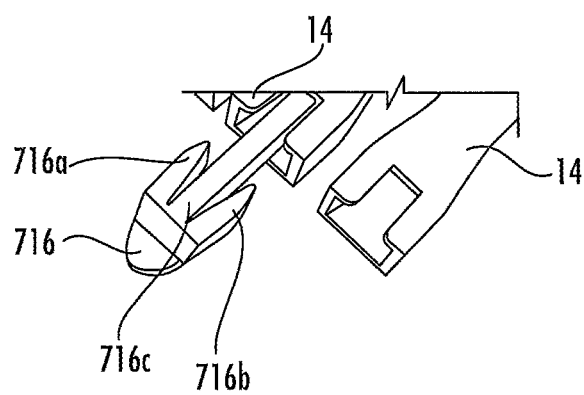
FIG. 12C is an isometric view of the hair grasping device of another embodiment.
Figure 12D:
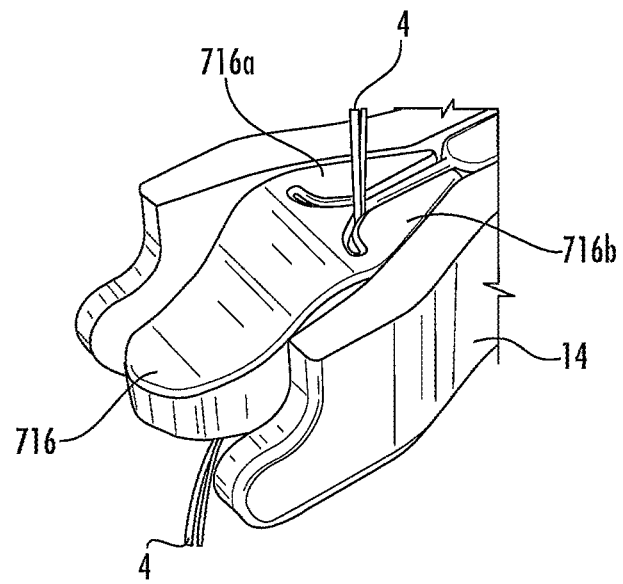
FIG. 12D is an isometric view of the hair grasping device of another embodiment.
Figure 12E:
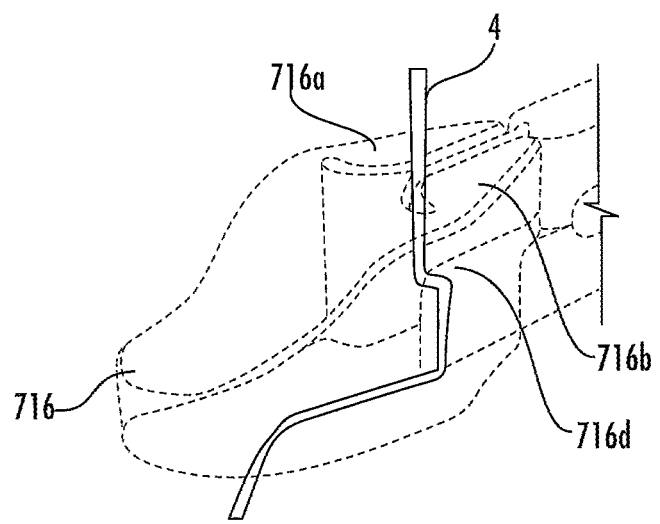
FIG. 12E is an isometric view of the hair grasping device of the embodiment of FIG. 12D with certain features hidden for clarity.
Figure 13:
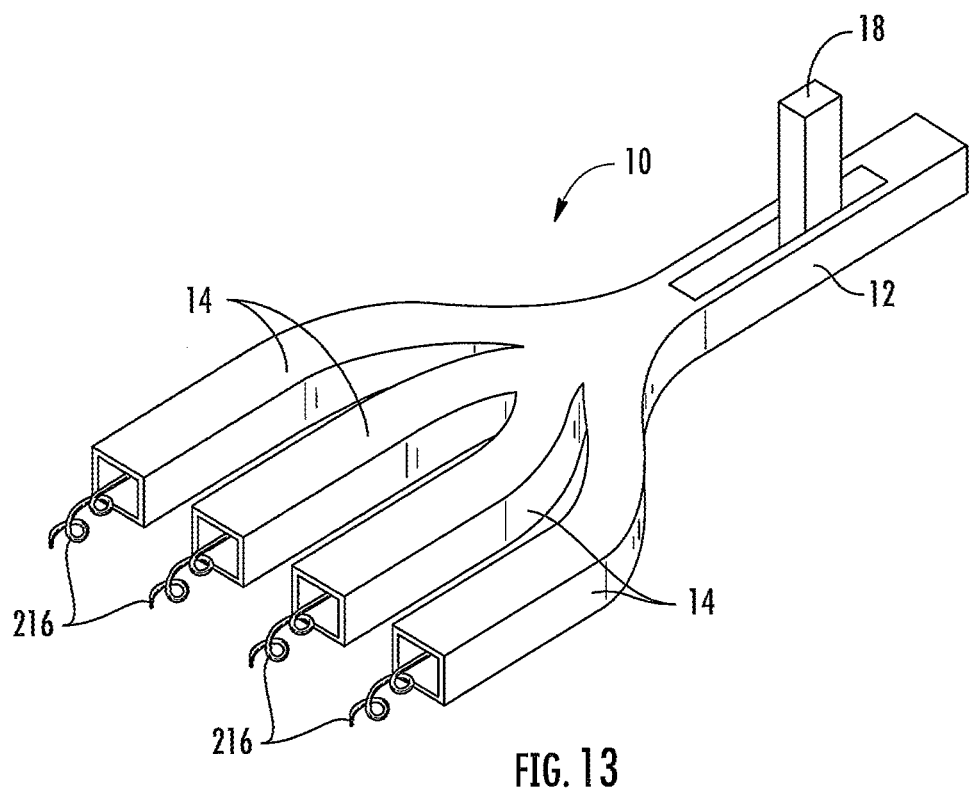
FIG. 13 is an isometric view of the hair grasping device of yet another embodiment.
Figure 14:
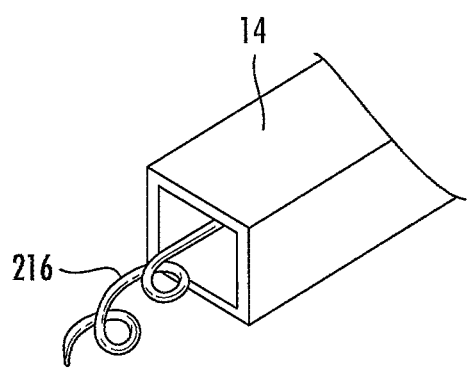
FIG. 14 is a close up isometric view of the grip and finger of the device shown in FIG. 13.

FIG. 12D shows what the grips 716 look like within the fingers 14 (shown transparent to better show the grips) with the hair 4 captured and in the retracted position. FIG. 12E is a transparent view showing the different planes of grip that the arms 716a, 716b and the center post 716c provide. These different planes, corners, and hair direction changes allow for greater pinching and holding force and prevents the hair from slipping through the grips 716 to allow sufficient pulling force to exceed the force required for wound closure.

Figure 34:
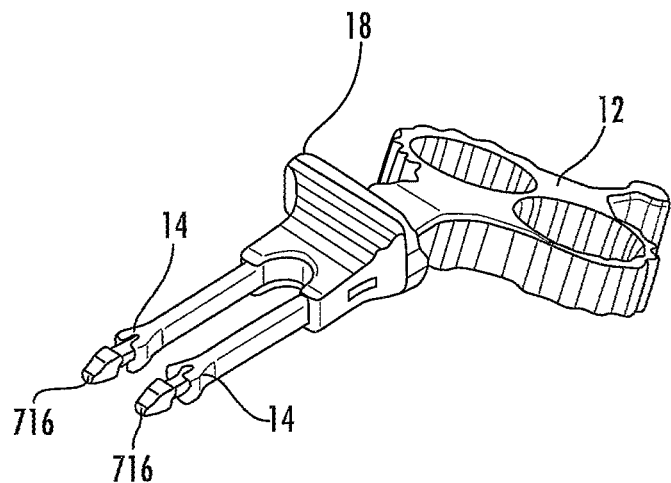
FIG. 34 is an isometric view of the hair grasping device of an embodiment.
Figure 35:
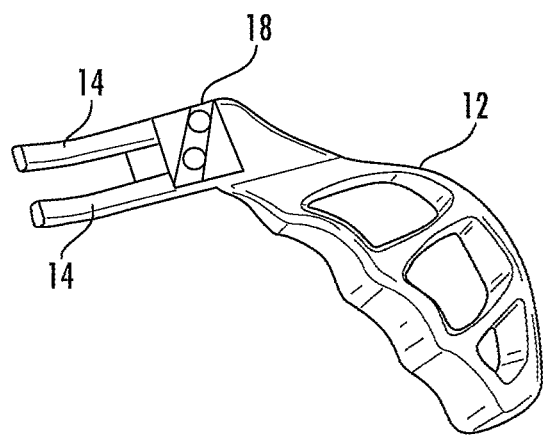
FIG. 35 is an isometric view of the hair grasping device of an embodiment.

FIGS. 34 and 35 show two different types of handles 12. FIG. 34 shows the device 10 with a two-finger handle, and the trigger 18 disposed on the top of the device 10. FIG. 35 shows the device 10 with a pistol grip, by which a user could hold the device 10 along a side rather than from the top. Different ring gripping angles and handle holding methods may be utilized to allow some fingers to remain free to stabilize the head or body part to allow wound closure. It is contemplated that different users may prefer fingers and grips that are rotated at any angle to better suit the user's specific preferences and needs.

FIGS. 13-16 show an embodiment that is similar to that of FIGS. 4-7. In this embodiment, the grips are screw-shaped grips 216. The device 10 operates in much the same way as the embodiment of FIGS. 4-7, however, instead of hooking an amount of hair 4 in a throat of a hook 16, the user works the screw grip 216 to capture an amount of hair in the screw-shape such that the hair 4 is wrapped around the screw 216. In the hair holding position, at least a portion of the screw grip 216 retracts within the finger 14 to hold the hair 4 in place by tension between the screw 216 and the inside wall of the fingers 14.

Figure 15:
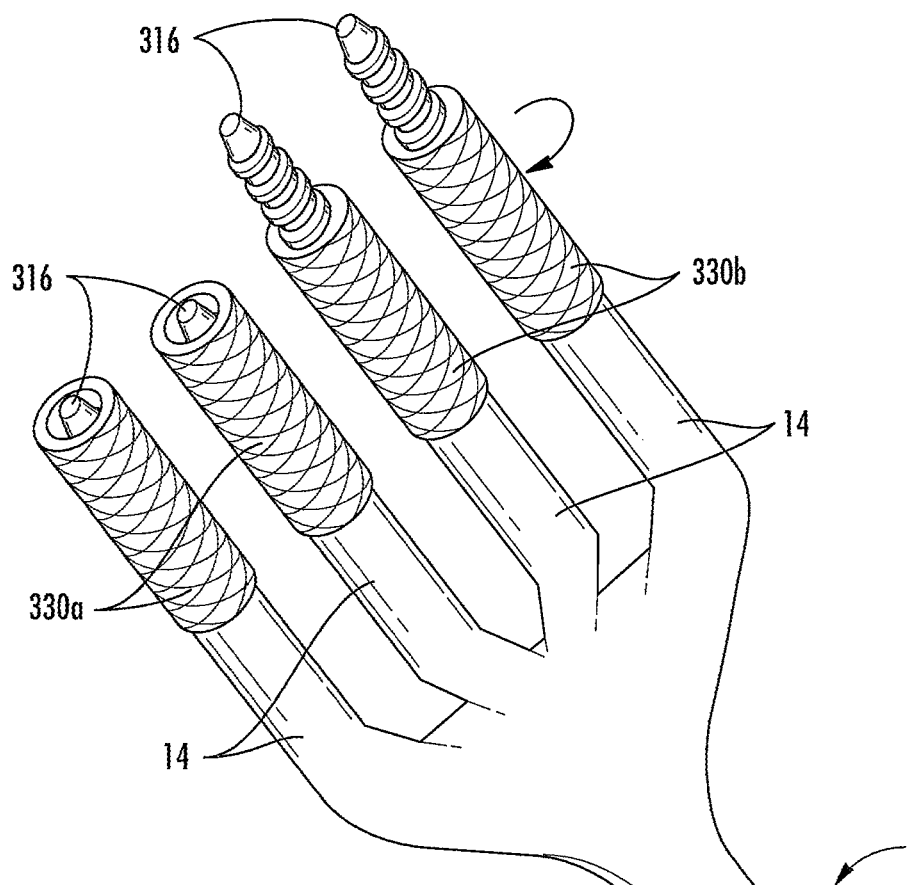
FIG. 15 is an isometric view of the hair grasping device of another embodiment.
Figure 16:
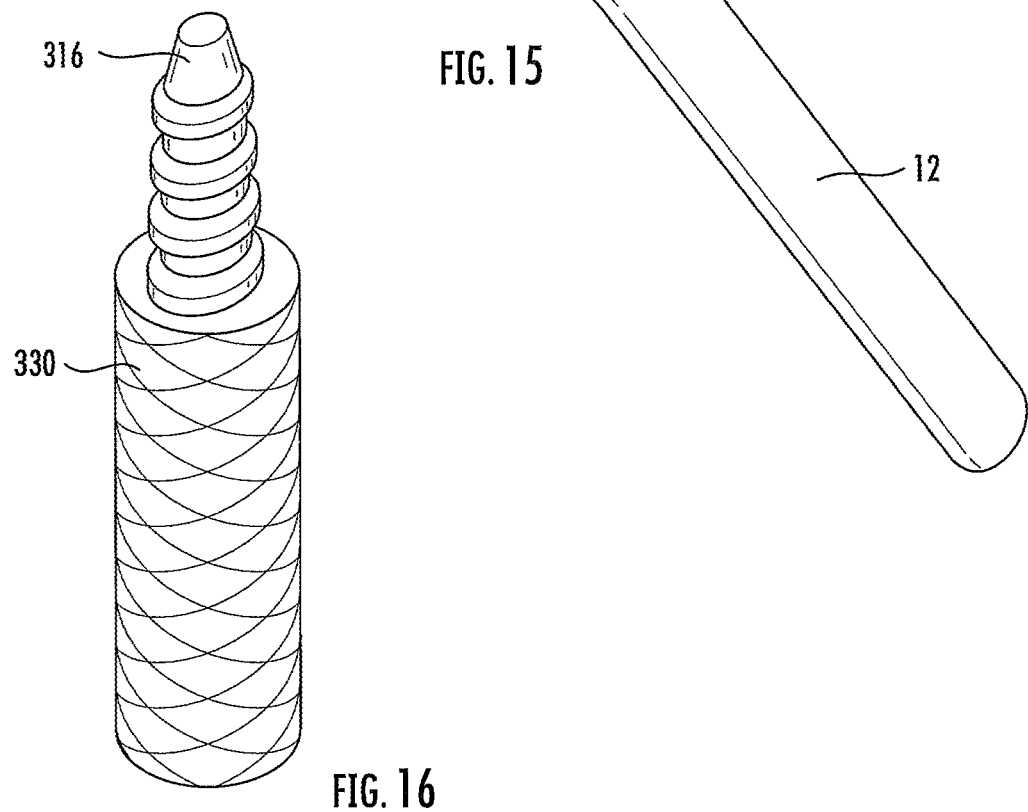
FIG. 16 is a close up isometric view of the grip and finger of the device shown in FIG. 15.

FIGS. 15-16 show an embodiment having a hair grip with external threads. The threaded grip 316 is linearly movably disposed within an internally threaded extrusion 330 that is rotatably disposed on the finger 14. In this embodiment, the trigger may be defined as the external surface of the extrusion 330, as that is the part manipulated by the user. The threaded grips 316 are externally threaded and associated with the internal threads of the extrusions 330. In the hair grasping position as shown by extrusions 330b, the threaded grips 316 are extended beyond the end of the extrusions 330. In the hair holding position, the threaded grips 316 are disposed within the extrusions 330. The hair 4 is held in place by tension between the threaded grips 316 and the interior walls of extrusions 330.

Figure 29:
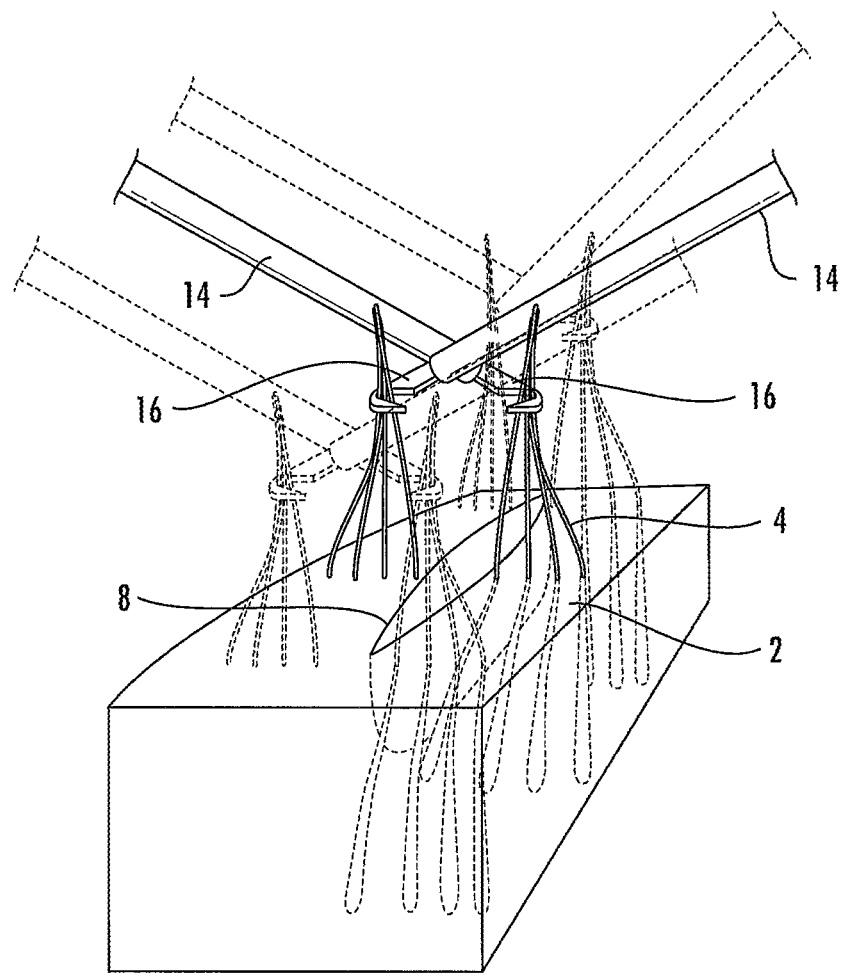
FIG. 29 is a schematic isometric view of the fingers and hooks of an embodiment of the hair grasping device.

In all of the embodiments of FIGS. 2-16, one device 10 may be used in conjunction with a second device 10 as shown in FIGS. 2C and 29. The fingers of each device 10 may be spaced apart such that the fingers of each device 10 fit between the fingers 14 of the other device 10, so that the devices 10 may be used simultaneously to grab an amount of hair 4 from one side of a laceration 8 and pull the hair 4 to an opposite side of the laceration 8.

Figure 17:
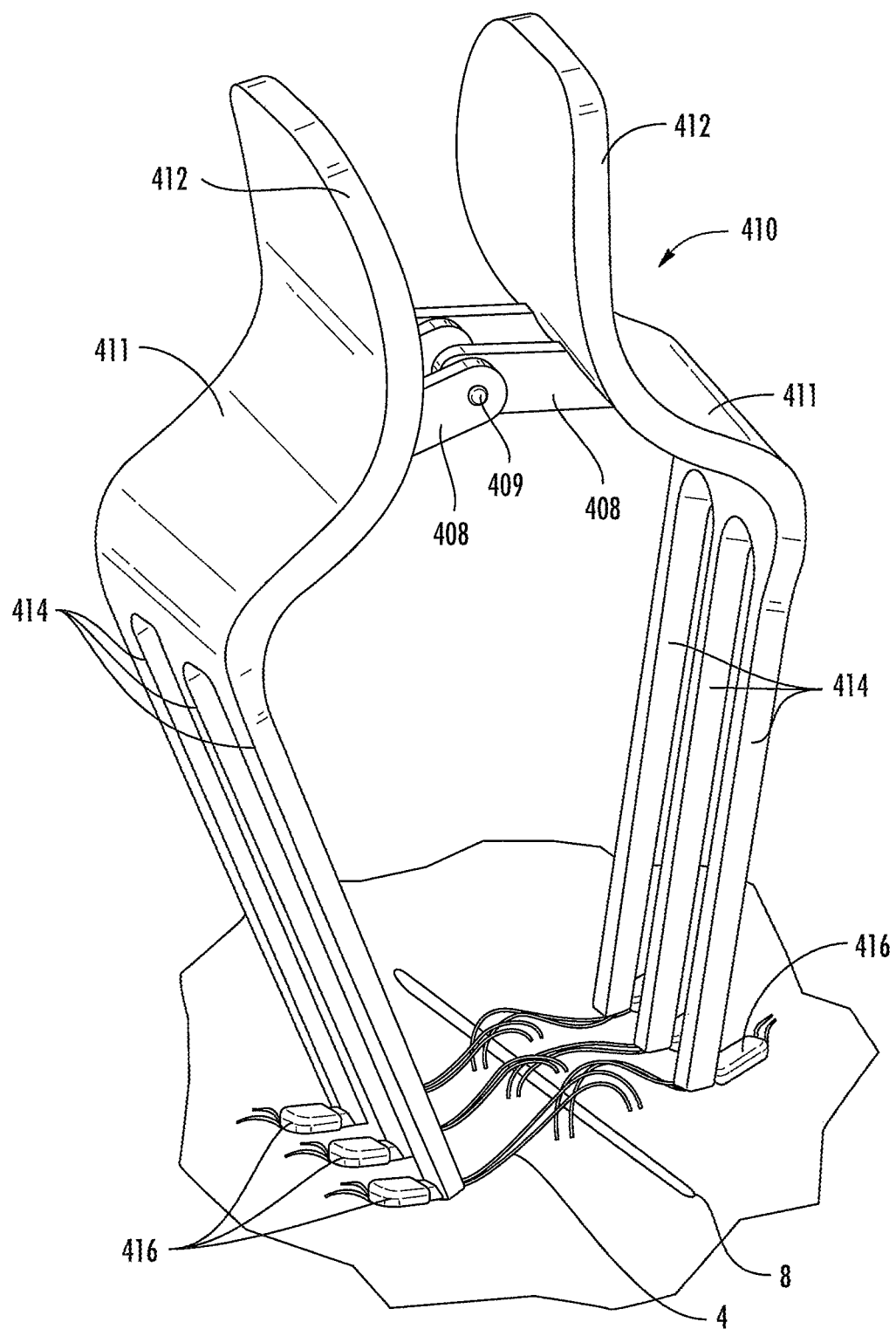
FIG. 17 is an isometric view of the hair grasping device of another embodiment.
Figure 20:
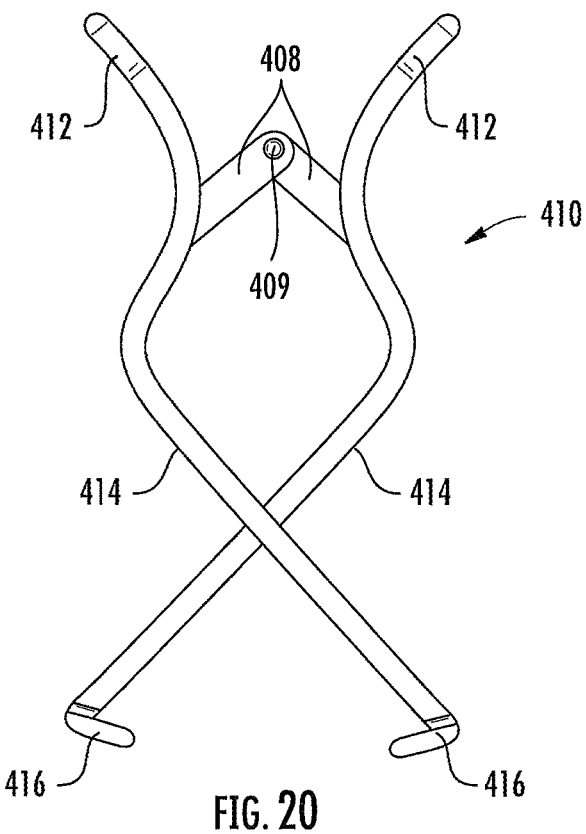
FIG. 20 is a side view of the hair grasping device of the shown in FIG. 17 in a hair grasping position.
Figure 21:
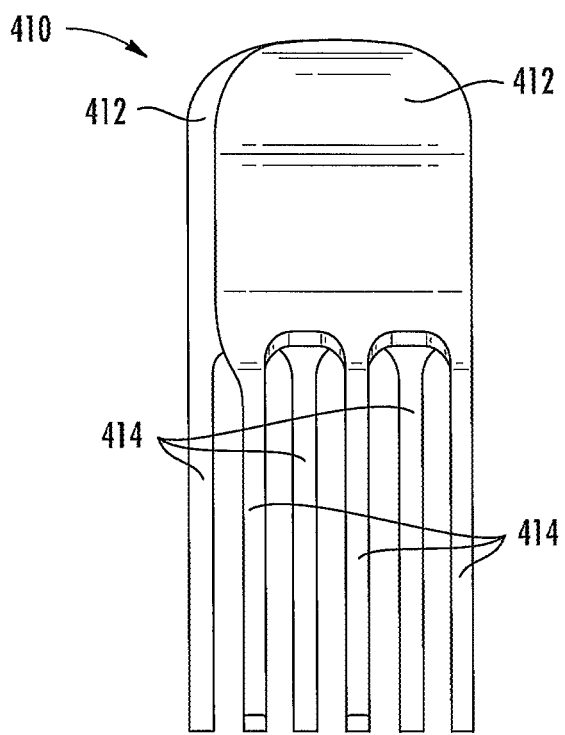
FIG. 21 is a front view of the hair grasping device of the shown in FIG. 17.

FIGS. 17-23 show an embodiment wherein a single device includes fingers 414 adapted to grab an amount of hair 4 on both sides of the laceration 8 at the same time and pull each respective amount of hair 4 across the laceration 8 to the other side. In this manner, the device disclosed in this embodiment may be operated by a user using a single hand. In FIG. 17, the hair grasping device 410 is made of arms 411 which have similar structure to the devices described above. Two arms 411 are substantially identical in structure (substantially identical in this respect may mean such minor differences based on manufacturing such as insubstantial molding differences or other post-molding differences) and are placed opposite one another. The two arms 411 are connected by and rotate with respect to one another about lever arms 408. The lever arms 408 may further include a pin 409 that holds the two arms 411 together and defines the axis about which each arm rotates. There may further be a spring (not shown) that urges the device into the hair grasping position. The hair grasping position in this embodiment is with the fingers 414 of the two arms 411 in a criss-cross configuration as shown in FIG. 20. FIG. 17 shows the device 410 in the hair holding position.

Figure 18:
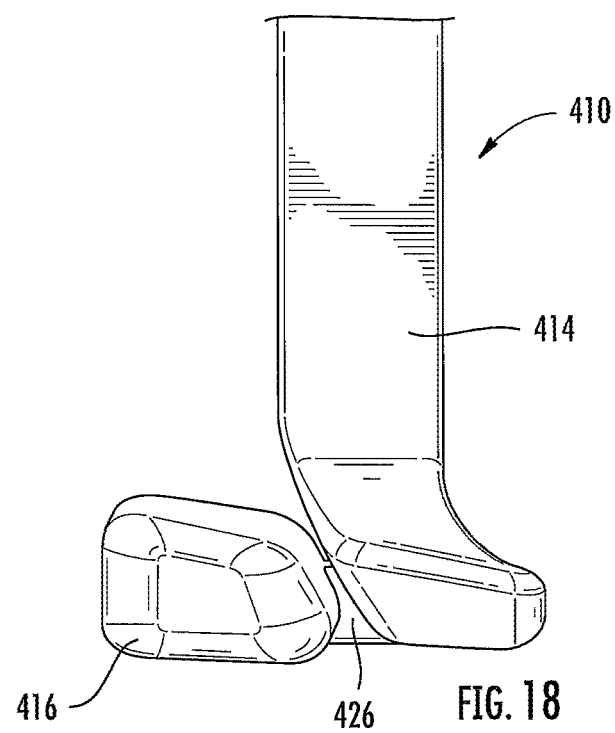
FIG. 18 is a close up isometric view of the grip and finger of the device shown in FIG. 17.
Figure 19:
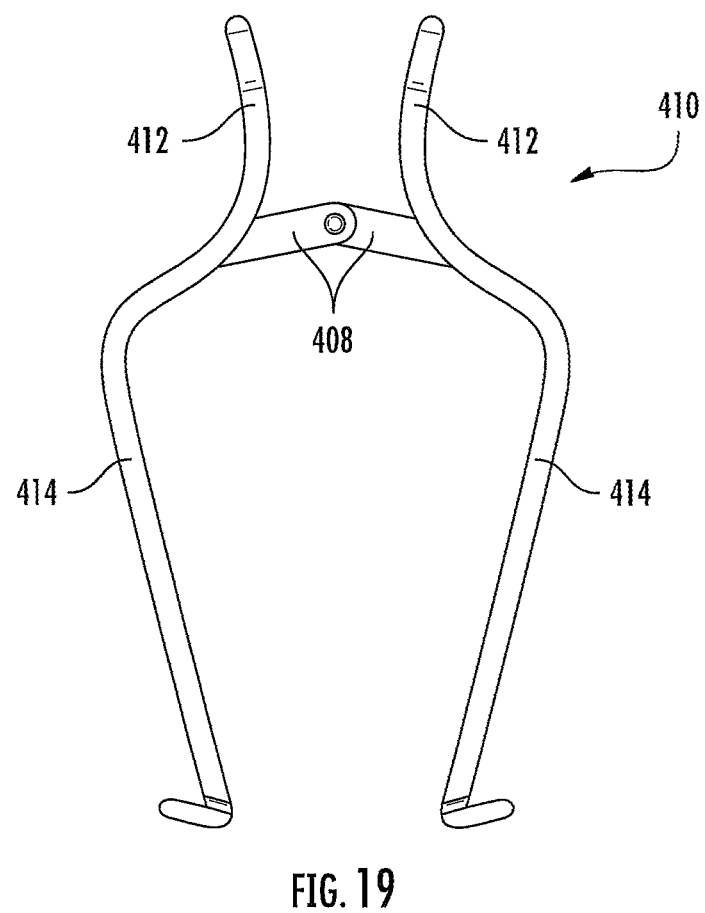
FIG. 19 is a side view of the hair grasping device of the shown in FIG. 17 in a hair holding position.

Turning now to FIG. 18, the device 410 has fingers 414 with hair grips on the ends of each of the fingers 414. The hair grips may include the hooks 16 or screw-shaped grips 216 described above. As shown, the grips 416 include a throat 426 defining a space between the grip 416 and the finger 414. The user may use one hand to grab the device 410. The user may place the device 410 such that fingers 414 from each of the arms 411 are lined up on opposite sides of a laceration 8. The user may then use a small twist motion to move an amount of hair 4 into the throat 426 of either side of the fingers 414. The twist motion may be necessary as the openings of the throat 426 face opposite directions when the device 410 is in use. The user may then squeeze the handles 412 of the two arms 411 together, which allows the fingers 414 of each arm 411 to cross to the opposite side of the laceration 8, as shown in FIG. 17. The user may then use these amounts of hair 4 to close up the wound. In another embodiment, an extrusion having an opening therein may be added to the fingers 414 to move relative to the fingers 414 and pinch the hair 4 in place, similar to the extrusions disclosed in the embodiments described above. Further, a cutting edge or blade may also be included within the hollow extrusion to cut the hair at the same time as it is being held in place.

Figure 22:
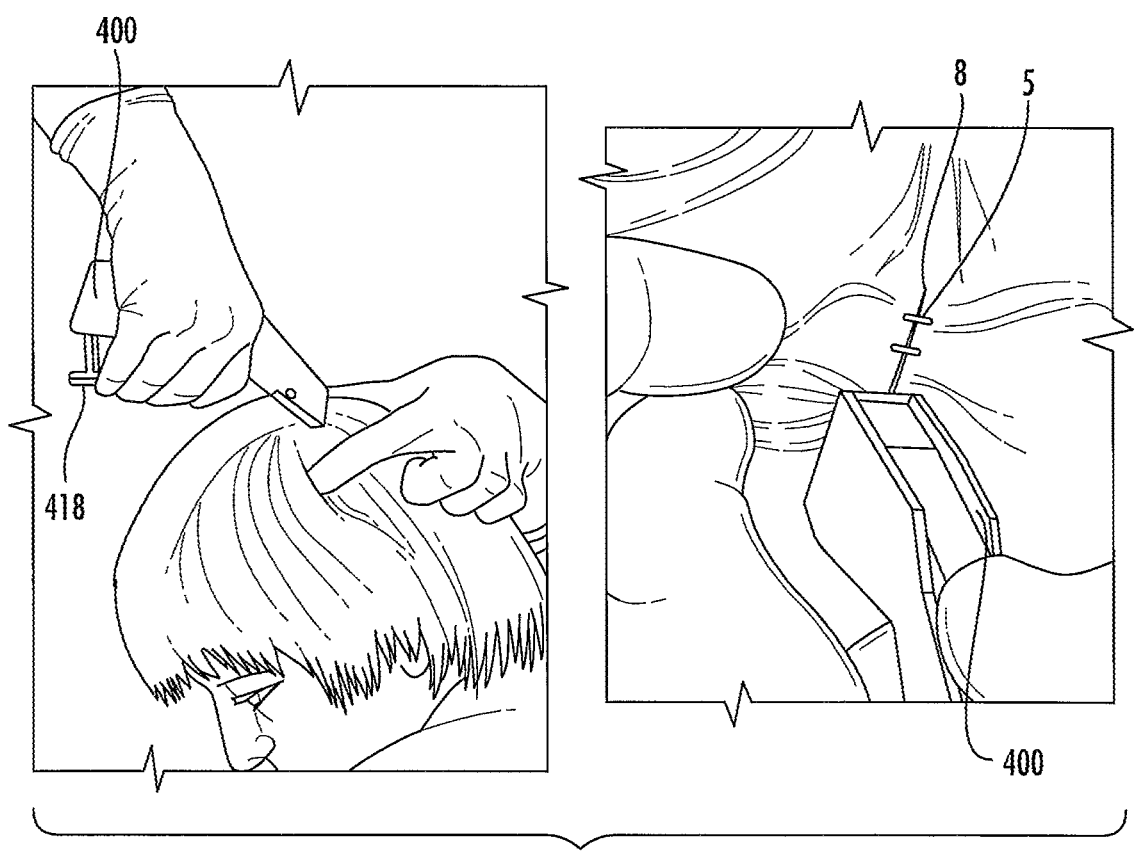
FIG. 22 is an isometric view of another embodiment of the hair grasping device which includes a single pair of opposing arms.
Figure 23:
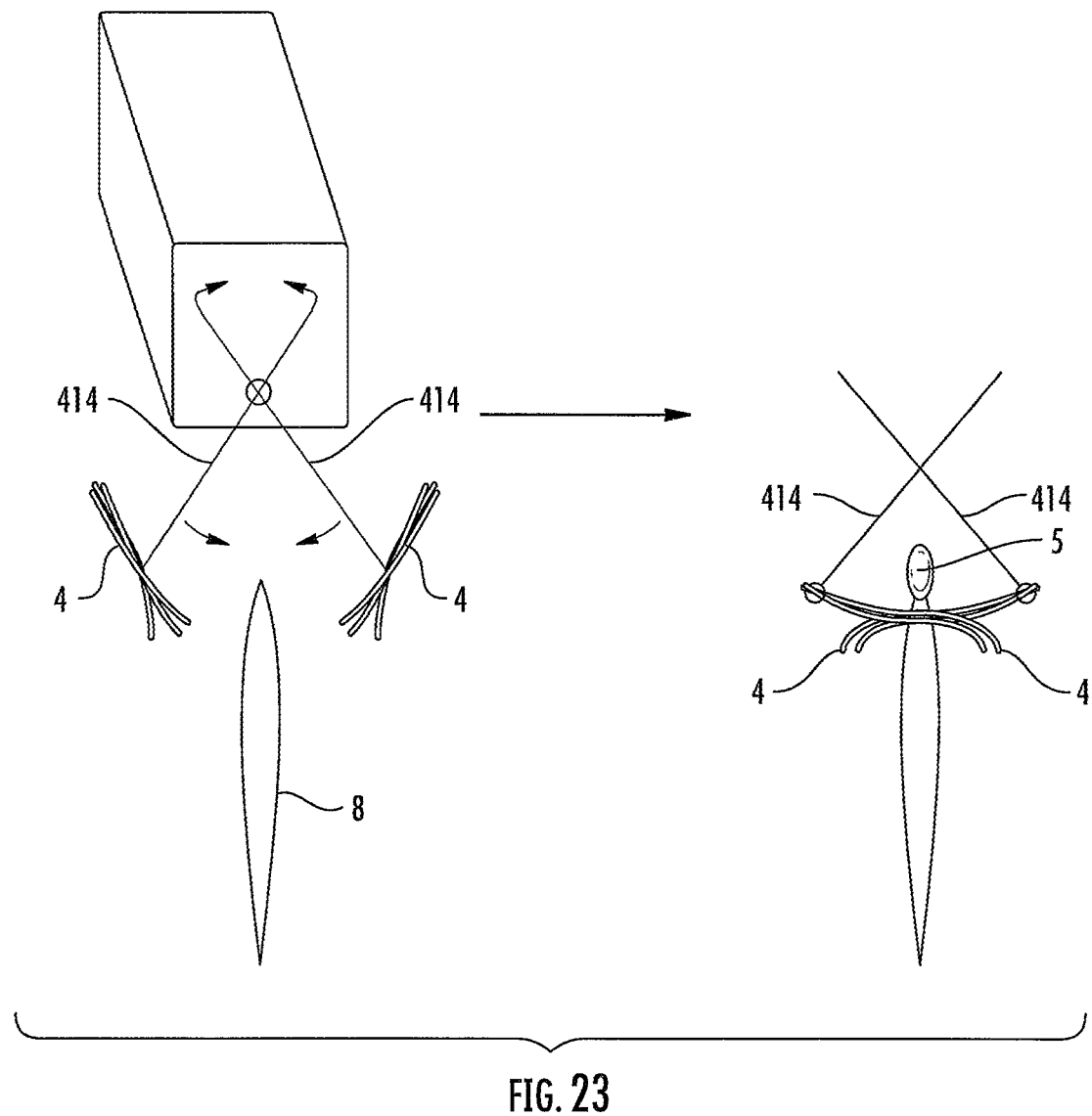
FIG. 23 is a schematic of the device shown in FIG. 22.

Additionally, as shown in FIGS. 22 and 23, a handheld device 400 may include similar structure as that shown in FIGS. 17-21, however with single fingers 414 on either side of the arms 411. The fingers 414 may be enclosed within a housing as shown in FIG. 22. The user may simply place the device 400 over a portion of the laceration 8 and allow the amounts of hair 8 to cross and automatically apply an amount of glue 5 to the area, as detailed in FIG. 23. The user may then move on to the next portion of the laceration and close the wound sequentially.

Figure 24:
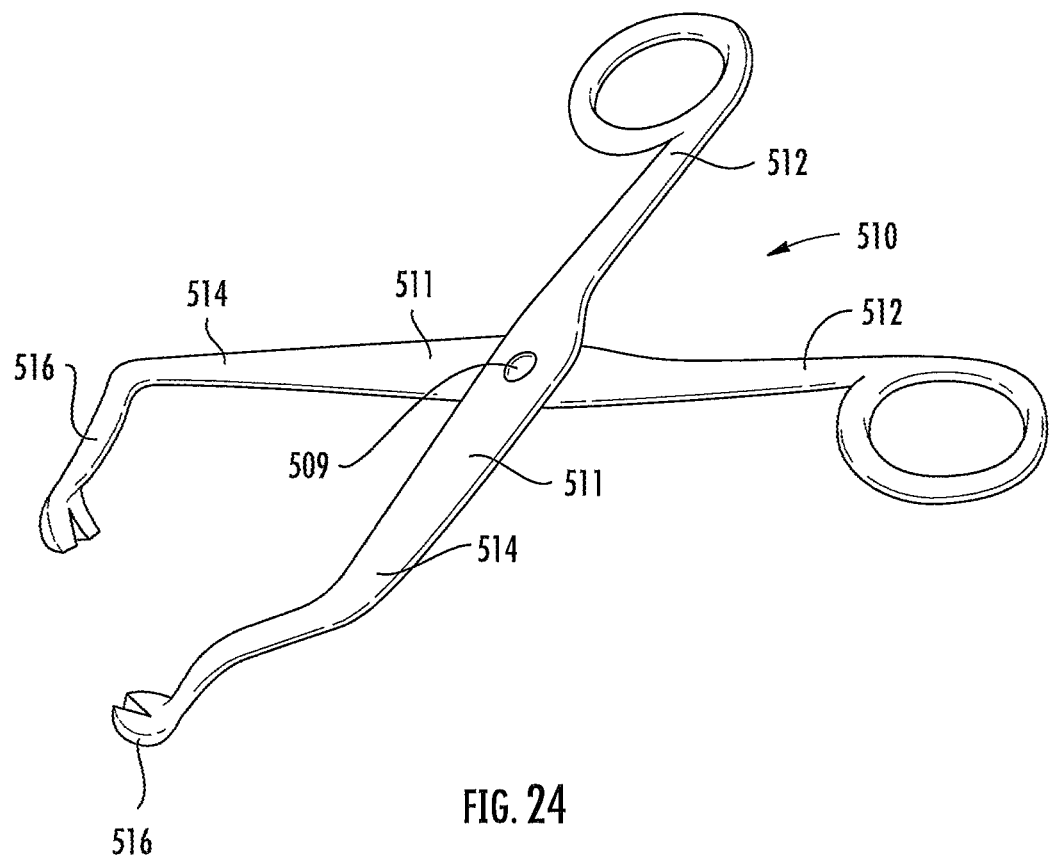
FIG. 24 is an isometric view of another embodiment of the hair grasping device in the hair grasping position.
Figure 25:
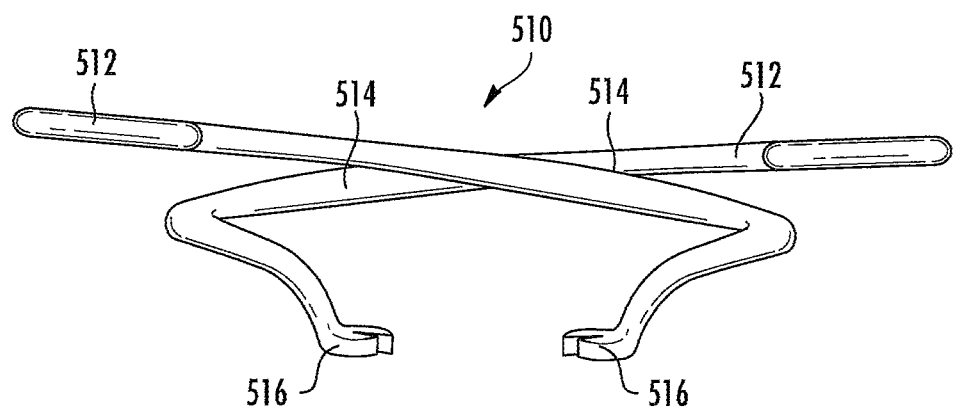
FIG. 25 is a side view of the hair grasping device shown in FIG. 24.

FIGS. 24-28 show another embodiment of the device 510 which may be operated by a single-hand of a user. In this embodiment, the device 510 is a scissor-like configuration. The device 510 may include a pair of arms 511 connected by and rotatable about a pin 509. In the hair grasping position as shown in FIG. 24, the user holds the handles 512 apart, which also holds the grips 516 apart, and positions the grips 516 on either side of the laceration 8. The user may then close the device 510 into the hair holding position as shown in FIG. 26, pulling amounts of hair 4 from one side of the laceration to the opposite side. The user may then use their other hand to apply glue 5 or other material to close that portion of the wound, before moving on closing to another portion of the laceration 8.

Figure 30A:
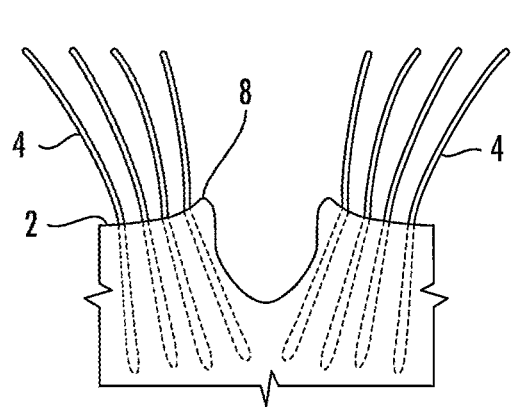
FIGS. 30A-30D are cross-sectional schematic views of a laceration of a patient as it is being closed using the device of an embodiment of the hair grasping device.
Figure 30B:
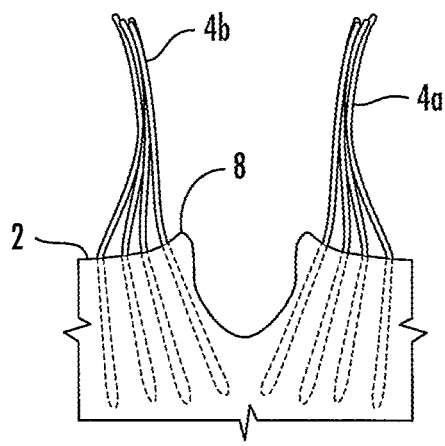
Figure 30C:
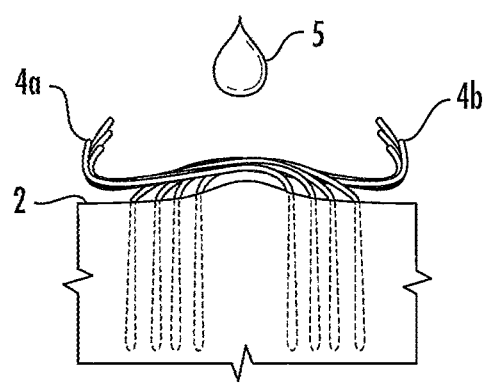
Figure 30D:
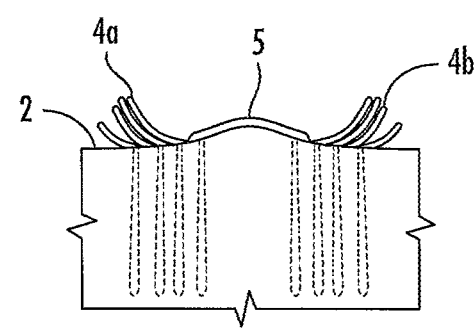
Figure 31:
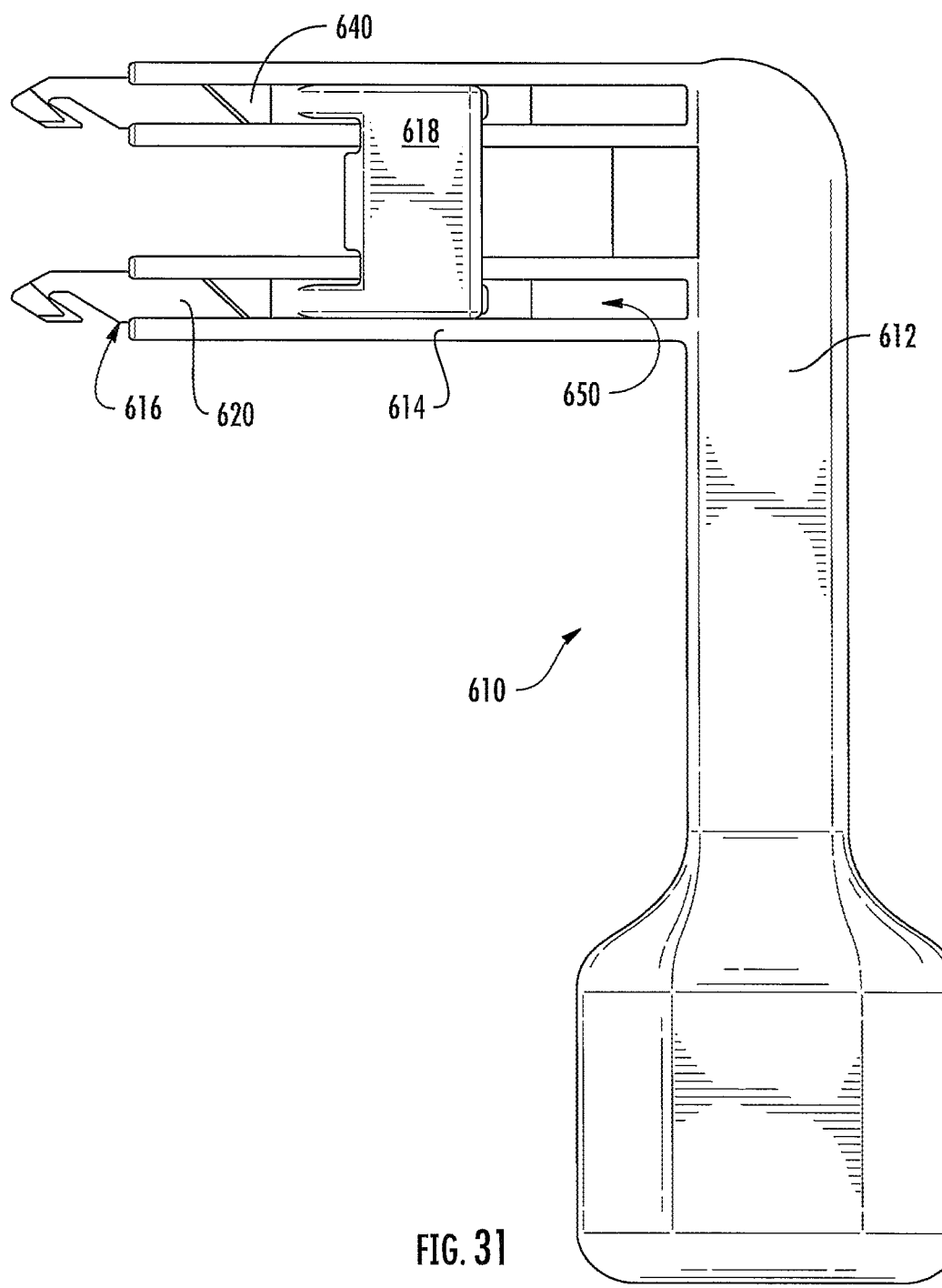
FIG. 31 is a top view of the hair grasping device of another embodiment.
Figure 32:
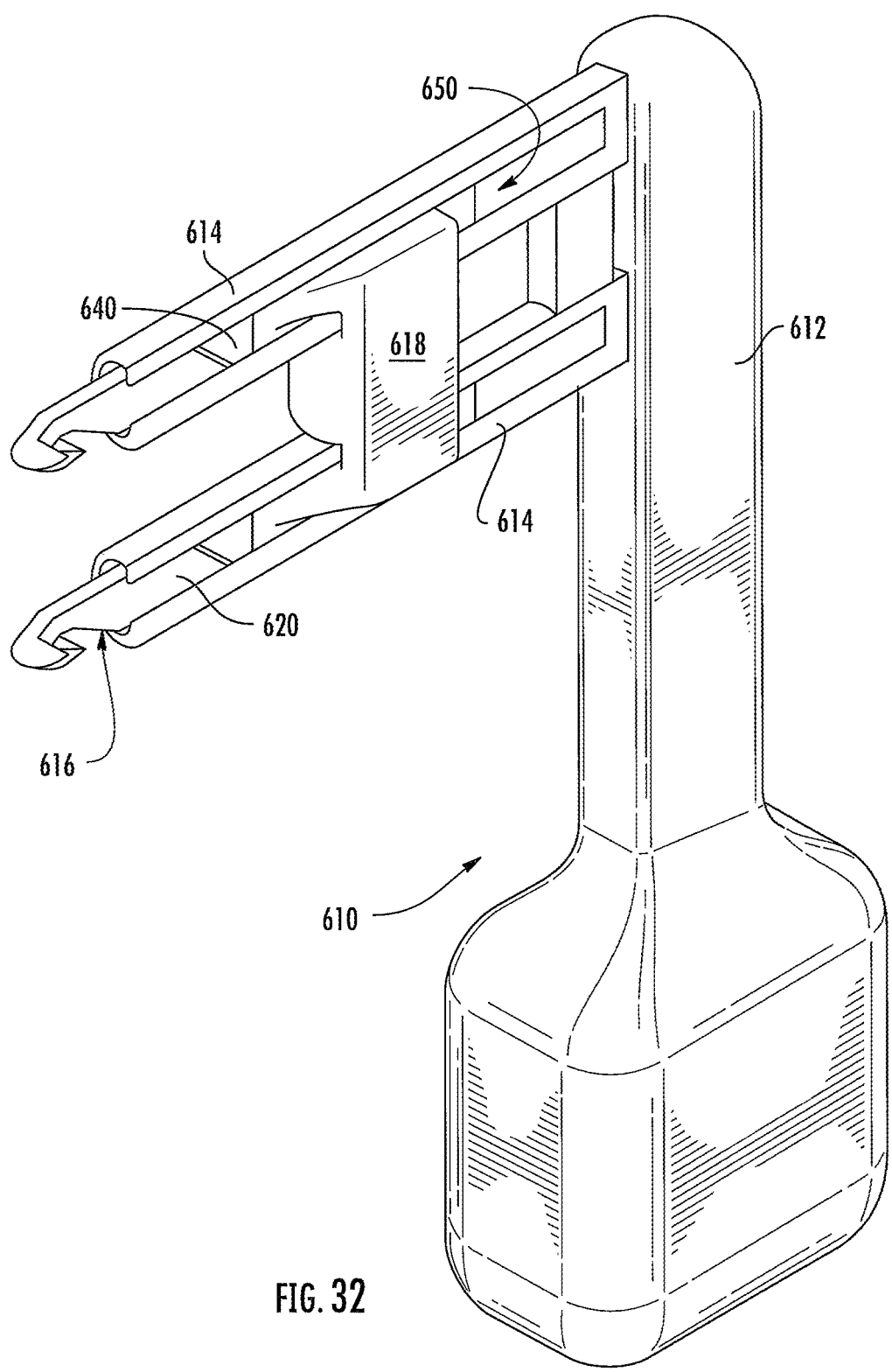
FIG. 32 is an isometric view of the hair grasping device of the embodiment.
Figure 33:
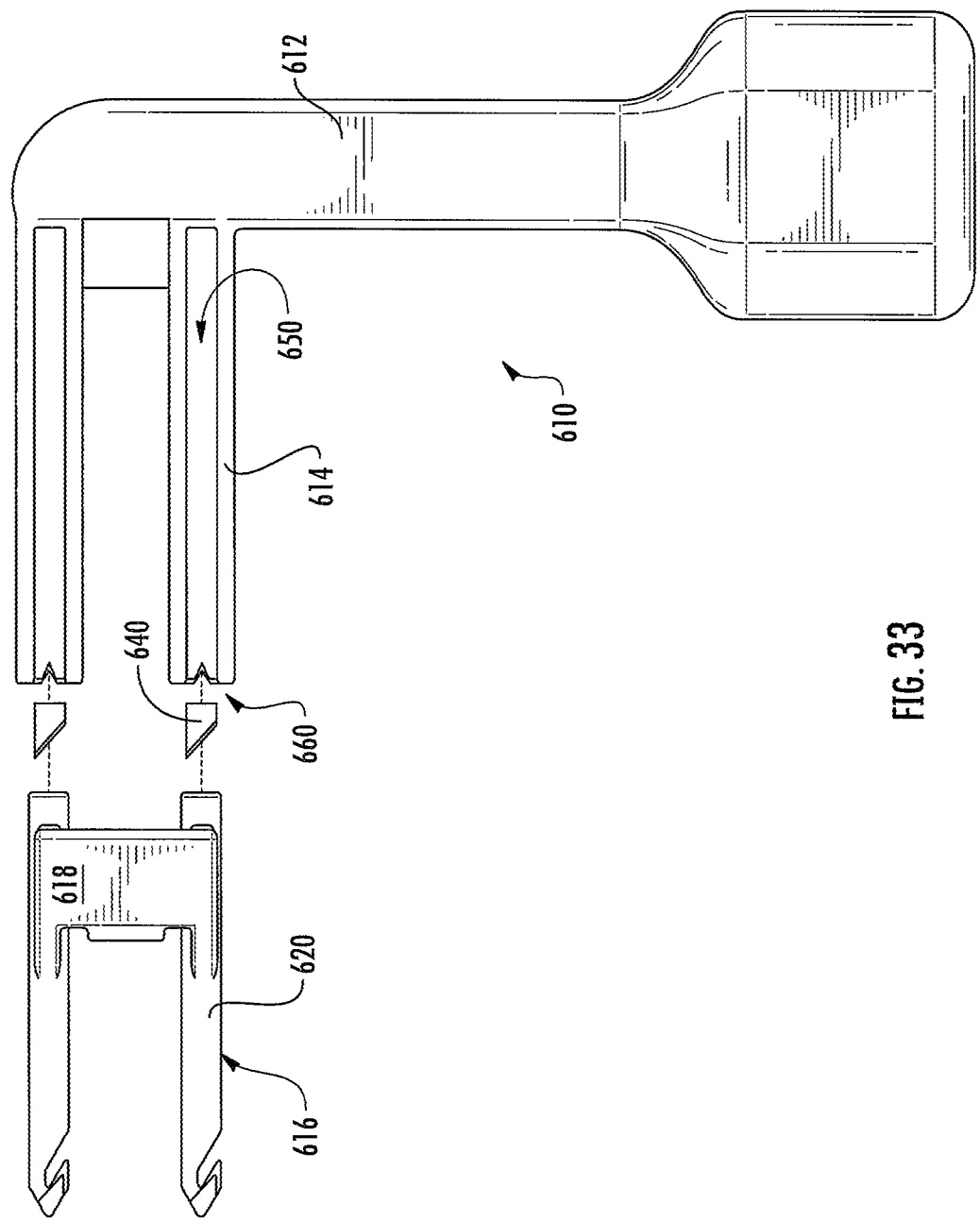
FIG. 33 is an exploded view of the hair grasping device of the embodiment.

Using any of the above described techniques, the hair apposition technique may be efficiently used to save the user and the patient time, discomfort, and expense. FIGS. 29-30D show in detail how the devices 10, 410, and 510 may aid the user in accomplishing the technique. FIG. 29 shows the fingers 14 of a device and the respective hair grips that are associated with the fingers 14. It should be noted that the fingers 14 and hair grips could apply to any of the fingers 14 or hair grips disclosed in any of the above embodiments.

As shown in FIG. 29, the hair grips grab an amount of hair 4 on opposite sides of a laceration 8. In some embodiments, two devices may be used at the same time to simultaneously pull hair 4 from opposite sides of the laceration 8 across the laceration 8. FIG. 30A shows a basic configuration of the hair 4 before the device 10 is presented to the area. FIG. 30B shows a basic configuration of the area after the hair 4 has been grasped by the device 10. FIG. 30C shows that when the opposite sides of the device are moved across the laceration 8, the hair pulls the laceration 8 closed, closing the wound. An amount of glue 5 or other material is presented to the area to hold it closed. Finally, once the glue 5 has settled and dried, the laceration 8 is held closed by the crossed amounts of hair 4 and held by the glue 5.

The above detailed description includes references to the accompanying drawing, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

It will be understood by one having ordinary skill in the art that construction of the described disclosure and other components is not limited to any specific material. Other exemplary embodiments of the disclosure disclosed herein may be formed from a wide variety of materials, unless described otherwise herein.

For purposes of this disclosure, the term "coupled" (in all of its forms, couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent in nature or may be removable or releasable in nature unless otherwise stated.

It is also to be understood that variations and modifications can be made on the aforementioned structures and methods without departing from the concepts of the present disclosure, and further it is to be understood that such concepts are intended to be covered by the following claims unless these claims by their language expressly state otherwise.

What is claimed is:

1. A method of closing a laceration, the method including the steps of:
   capturing an amount of hair between a pair of arms of a grip while the pair of arms are in an open position;
   sliding the pair of arms into an internal opening within a hollow finger of a hair grasping device by operably sliding a trigger disposed on a handle on the hair grasping device from a released position to a grasping position;
   ensnaring the amount of hair by urging the pair of arms to a closed position by retracting the pair of arms within the hollow finger; and
   holding the amount of hair by exerting a pinching force on the arms by the internal opening.

2. The method of claim 1 further comprising the step of extending the pair of arms from the hollow finger by releasing the trigger, allowing a biasing force on the trigger to move the trigger from the grasping position to the released position.

3. The method of claim 1 wherein the sliding the pair of arms step is accomplished by pulling the trigger toward a user.

4. The method of claim 1 wherein the hair grasping device comprises two hollow fingers and two grips slidably disposed within the two hollow fingers.

5. The method of claim 4, further comprising a second hair grasping device comprising two hollow fingers and two grips slidably disposed within the two hollow fingers of the second grasping device, and wherein the fingers of each of the hair grasping device and the second hair grasping device fit between one another, and wherein the hair grasping device and the second hair grasping device are used simultaneously to grasp hair on opposite sides of a laceration.

6. A method of closing a laceration using hair on opposite sides of the laceration, the method including the steps of:
   capturing a first amount of hair on a first side of a laceration in a first grip between an arm of a first grip and a first finger;
   capturing a second amount of hair on a second side of the laceration opposite the first side in a second grip, the second amount of hair being captured between an arm of a second grip and a second finger;
   closing the laceration by pulling the first amount of hair to the second side and the second amount of hair to the first side; and
   applying an amount of glue to the closed laceration.

7. The method of claim 6, wherein the capturing a first amount of hair step further comprises the steps of:
   capturing the first amount of hair within the arm of the first grip when the first grip is in an open position then moving the first grip to a closed position, preventing the first amount of hair from slipping out of the first grip by holding the first amount of hair between the arm of the first grip and the first finger; and wherein the capturing a second amount of hair step further comprises the steps of:

capturing the second amount of hair within the arm of the second grip when the second grip is in an open position then moving the second grip to a closed position, preventing the second amount of hair from slipping out of the second grip by holding the second amount of hair between the arm of the second grip and the second finger.

8. The method of claim 6, wherein the capturing a first amount of hair step further comprises the steps of:

capturing the first amount of hair within the arm of the first grip when the first grip is in an open position then moving the first finger along the first grip to a closed position, preventing the first amount of hair from slipping out of the first grip by holding the first amount of hair between the arm of the first grip and the first finger; and wherein the capturing a second amount of hair step further comprises the steps of:

capturing the second amount of hair within the arm of the second grip when the second grip is in an open position then sliding the second finger along the second grip to a closed position, preventing the second amount of hair from slipping out of the second grip by holding the second amount of hair between the arm of the second grip and the second finger.

9. A method of closing a laceration, the method including the steps of:

providing a first hair grasping device having a first finger with a first longitudinal axis and a first gripping portion slidable on the first finger along the first longitudinal axis, and a second hair grasping device having a second finger with a second longitudinal axis and a second gripping portion slidable on the second finger along the second longitudinal axis;

moving the first gripping portion with respect to the first finger of the first hair grasping device to an open position;

placing a first amount of hair on a first side of a laceration within the first gripping portion while the first gripping portion is in the open position;

holding the first amount of hair within the first gripping portion by sliding the first gripping portion from the open position to a grasping position;

moving the second gripping portion with respect to the second finger of the second hair grasping device to an open position;

placing a second amount of hair on a second side of the laceration within the second gripping portion while the second gripping portion is in the open position;

holding the second amount of hair within the second gripping portion by sliding the second gripping portion from the open position to a grasping position;

pulling the first amount of hair to the second side of the laceration; and pulling the second amount of hair to the first side of the laceration.

10. The method of claim 9, wherein the first hair grasping device comprises a third gripping portion slidable along a third longitudinal axis of a third finger, and further comprising the steps of:

moving the third gripping portion with respect to the third finger of the first hair grasping device to an open position;

placing a third amount of hair on the first side of the laceration within the third gripping portion while the third gripping portion is in the open position; and holding the third amount of hair within the third gripping portion by sliding the third gripping portion from the open position to a grasping position.

11. The method of claim 10, wherein the second hair grasping device comprises a fourth gripping portion slidable along a fourth longitudinal axis of a fourth finger, and further comprising the steps of:

moving the fourth gripping portion with respect to the fourth finger of the second hair grasping device to an open position;

placing a fourth amount of hair on the second side of the laceration within the fourth gripping portion while the fourth gripping portion is in the open position; and holding the fourth amount of hair within the fourth gripping portion by moving the fourth gripping portion from the open position to a grasping position.

12. The method of claim 9 wherein the first gripping portion comprises a pair of arms; and wherein the holding the first amount of hair step is accomplished by:

sliding the pair of arms of the first gripping portion into an internal opening within the first finger of the first hair grasping device by sliding a trigger disposed on a handle of the first hair grasping device from a released position to a grasping position, closing the pair of arms about the first amount of hair.

13. The method of claim 12 wherein the second gripping portion comprises a pair of arms; and wherein the holding the second amount of hair step is accomplished by:

sliding the pair of arms of the second gripping portion into an internal opening within the second finger of the second hair grasping device by operably sliding a trigger disposed on a handle of the second hair grasping device from a released position to a grasping position, closing the pair of arms about the second amount of hair.

14. The method of claim 9, wherein:

the first hair grasping device comprises a third gripping portion slidable along a third longitudinal axis of a third finger;

the first gripping portion comprises a first hook and the third gripping portion comprises a third hook;

the first hair grasping device further comprises a trigger operably connected to the first and third gripping portion; and further comprising the steps of:

moving the third gripping portion with respect to the third finger of the first hair grasping device to an open position;

placing a third amount of hair on the first side of the laceration within the third gripping portion while the third gripping portion is in the open position; and holding the third amount of hair within the third gripping portion by moving the first gripping portion and the third gripping portion from the open position to a grasping position by operating the trigger.

15. The method of claim 14, wherein the trigger is slidably attached to the first and third fingers along the first and third longitudinal axes.

* * * * *